United States Patent
Amico et al.

(10) Patent No.: US 10,255,521 B2
(45) Date of Patent: Apr. 9, 2019

(54) SYSTEM, METHOD, AND APPARATUS FOR DETECTION OF DAMAGES ON SURFACES

(71) Applicant: Jack Cooper Logistics, LLC, Kennesaw, GA (US)

(72) Inventors: Andrea Amico, Marietta, GA (US); Mohit Prabhushankar, Atlanta, GA (US)

(73) Assignee: Jack Cooper Logistics, LLC, Kennesaw, GA (US)

( * ) Notice: Subject to any disclaimer, the term of this patent is extended or adjusted under 35 U.S.C. 154(b) by 196 days.

(21) Appl. No.: 15/375,895

(22) Filed: Dec. 12, 2016

(65) Prior Publication Data

US 2018/0165541 A1    Jun. 14, 2018

(51) Int. Cl.
*G06K 9/62* (2006.01)
*H04N 5/232* (2006.01)
(Continued)

(52) U.S. Cl.
CPC ....... *G06K 9/6212* (2013.01); *G01N 21/8851* (2013.01); *G06K 9/2027* (2013.01);
(Continued)

(58) Field of Classification Search
CPC .......... G06K 9/6212; G06K 9/44; G06K 9/38; G06K 9/4661; G06K 9/4652; H04N 1/6002; H04N 9/045; H04N 5/2256; H04N 9/67; H04N 5/23222; G06T 5/002; G06T 7/60; G06T 2207/30252; G06T 2207/10016;
(Continued)

(56) References Cited

U.S. PATENT DOCUMENTS 4,629,319 A    12/1986  Clark et al.
5,436,726 A    7/1995   Ventura et al.
(Continued)

FOREIGN PATENT DOCUMENTS

WO    WO 2009/060536    5/2009
WO    WO 2015/080941    6/2015

OTHER PUBLICATIONS

Lilienblum, Tilo et al., "Dent Detection in Car Bodies," Proceedings of the International Conference on Pattern Recognition (ICPR'00) 1054-4651, 2000.
(Continued)

*Primary Examiner* — Zaihan Jiang
(74) *Attorney, Agent, or Firm* — King & Spalding

(57) ABSTRACT

A portable computing device equipped with at least one image capture device and/or a light source captures an image (or a video) of a portion of a surface of interest having the damage that is exposed to a light from the light source. The portable computing device converts the image to an output image that highlights the damage. If the damage is a dent, the image is converted to a false color image using a saliency algorithm. If the damage is a scratch, the image is converted to a colorspace stretched image using color stretching algorithms. The size of the damage is determined by capturing an image of a ruler placed adjacent to the damage and the portion of surface of interest having the damage. The ruler is then removed from the image. The resulting image is converted to the output image. The ruler is added to the output image.

24 Claims, 17 Drawing Sheets

(51) Int. Cl.
*H04N 1/60* (2006.01)
*H04N 9/04* (2006.01)
*H04N 5/225* (2006.01)
*H04N 9/67* (2006.01)
*G06K 9/38* (2006.01)
*G06K 9/46* (2006.01)
*G06T 5/00* (2006.01)
*G06T 7/60* (2017.01)
*G06K 9/44* (2006.01)
*G01N 21/88* (2006.01)
*G06K 9/20* (2006.01)
*G06K 9/22* (2006.01)
*G06T 7/00* (2017.01)
*G06K 9/52* (2006.01)

(52) U.S. Cl.
CPC ............ *G06K 9/22* (2013.01); *G06K 9/4652* (2013.01); *G06K 9/4671* (2013.01); *G06T 7/0004* (2013.01); *H04N 1/6002* (2013.01); *H04N 5/23222* (2013.01); *H04N 5/23229* (2013.01); *H04N 5/23293* (2013.01); *H04N 9/67* (2013.01); *G06K 9/4661* (2013.01); *G06K 9/52* (2013.01); *G06T 2207/10016* (2013.01); *G06T 2207/10024* (2013.01); *G06T 2207/30108* (2013.01); *H04N 5/2256* (2013.01)

(58) Field of Classification Search
CPC .......... G06T 2207/10004; G06T 2207/10024; G01N 21/8851
USPC ........................................................ 348/128
See application file for complete search history.

(56) References Cited

U.S. PATENT DOCUMENTS

| | | | |
|---|---|---|---|
| 5,572,324 A | 11/1996 | Ventura | |
| 5,680,215 A * | 10/1997 | Huber | G01B 11/306 356/237.1 |
| 5,818,593 A | 10/1998 | Ventura | |
| 5,825,495 A * | 10/1998 | Huber | G01B 11/306 356/600 |
| 6,320,654 B1 | 11/2001 | Alders et al. | |
| 8,527,140 B2 | 9/2013 | Schwartz | |
| 9,886,771 B1 * | 2/2018 | Chen | G06T 7/0032 |
| 2004/0093100 A1 * | 5/2004 | Gleis | G05B 19/41875 700/95 |
| 2007/0067075 A1 | 3/2007 | McMillan et al. | |
| 2007/0146728 A1 | 6/2007 | Pristner | |
| 2008/0063237 A1 * | 3/2008 | Rubenstein | G06K 9/0063 382/103 |
| 2008/0183535 A1 * | 7/2008 | Kahana | G06Q 30/06 705/37 |
| 2013/0201210 A1 | 8/2013 | Vaddadi et al. | |
| 2013/0208105 A1 * | 8/2013 | Schmidt | G01N 21/9054 348/92 |
| 2013/0215093 A1 * | 8/2013 | Bergquist | G09G 3/3208 345/207 |
| 2014/0118561 A1 * | 5/2014 | La Lumondiere | G01N 21/9505 348/207.1 |
| 2014/0201022 A1 | 7/2014 | Balzer | |
| 2014/0313334 A1 | 10/2014 | Slotky | |
| 2015/0036924 A1 * | 2/2015 | Kuusisto | G06K 9/4638 382/165 |
| 2015/0321605 A1 | 11/2015 | Mirza et al. | |
| 2016/0100087 A1 | 4/2016 | Scheich | |
| 2017/0032170 A1 * | 2/2017 | Bazrafkan | G06K 9/00026 |
| 2017/0148102 A1 * | 5/2017 | Franke | G06Q 10/20 |
| 2018/0017504 A1 * | 1/2018 | Freiberger | G01N 21/9054 |

OTHER PUBLICATIONS

Jayawardena, Srimal, "Image Based Automatic Vehicle Damage Detection," A thesis submitted for the degree of Doctor of Philosophy at The Australian National University, Nov. 2013.

\* cited by examiner

SYSTEM, METHOD, AND APPARATUS FOR DETECTION OF DAMAGES ON SURFACES

TECHNICAL FIELD

The present disclosure relates generally to computer vision, and in particular to a system, method, and apparatus for detection of damages on surfaces using computer based image processing and analysis.

BACKGROUND

Goods and products that have reflective surfaces (or have surfaces with reflective coating), such as painted metals, painted plastic, opaque glasses, reflective coated furniture, etc., and/or non-reflective surfaces or partially-reflective surfaces, such as matte surfaces with limited surface roughness, matte plastics, wood, etc., may get damaged during operation or transportation of the goods and products. Some of said goods and products may be insured to compensate the costs associated with the damages. Claims management companies currently require photographic evidence of the damages to document the extent of the damages and to claim compensation for the damages. Typically, upon receiving a photograph of the damaged surface, an employee of the claims management company may examine the photograph with his/her naked eye and document the extent of damage based on an estimation made by the employee. Such estimation of the extent of the damages may be subjective and may vary from person to person. Further, more often than not, the extent of the damages may be underestimated or overestimated due to human error.

Additionally, in the case of highly reflective surfaces, additional issues may arise with traditional photographs. Specifically, the reflective nature of the surfaces may result in photographs having considerable amount of reflection and/or may make it difficult for camera sensors to appropriately focus the picture. The resulting reflections and/or poor focus in the photographs render the photograph ineffective for detection and estimation of the extent of the damages as they prevent a clear and effective view of the damages. In such cases, the photographic evidences end up mostly being a formality rather than their intended purpose of providing hard evidence regarding the extent of the damages. Furthermore, proportional to the size of the damages, the ability to detect and capture the damages in a photograph becomes hard because of the reflections from the reflective surfaces. In other words, smaller damages are not easily detectable by the naked eye let alone be captured and detected in a photograph because of reflections from the reflective surfaces.

Automated technology, such as computer vision, that moves the process of detecting and determining the extent of the damages away from a human user does exist. However, in many cases, the considerable amount of reflection in the photographs and/or poor focus render standard computer vision-based technologies incapable of detecting and estimating the extent of the damages. Other technologies for reducing the amount of reflection from the reflective surface exist as well. However, said existing technologies may require special lighting and set-up, such as structured light equipment, lasers, multiple specialized cameras, controlled reflection environments, etc., which makes them both cost-intensive and time-intensive. Further, the specialized set-up and the operation of the specialized lighting may require highly skilled personal that is adept in operating the specialized equipment.

In light of the above deficiencies of existing technology, there exists a need for an improved automated technology for detecting and estimating the extent of damages on a reflective surface.

SUMMARY

The present disclosure describes an improved digital image processing and analysis system, method, and/or apparatus that provides a technical solution rooted in computer vision technology to address one or more technical problems of existing automated damage detection technology, such as, the inability of standard computer vision technology to accurately detect smaller damages and/or to estimate the extent of said damages on a reflective surface using digital images of the reflective surface captured under variable lighting conditions.

In one example aspect, the system, method, and apparatus described herein for detection of damages on a surface of interest, e.g., reflective surface, may include a portable computing device that is equipped with one or more of the following: (i) a light source (e.g., flash) configured to illuminate a surface of interest, (ii) one or more cameras configured to capture a digital image or video of a damage on the surface of interest, (iii) a display configured to render an image or video feed received from the one or more cameras (e.g., camera sensors) and/or to present other appropriate images or video, (iv) a processor configured to process and analyze captured images or video of the surface of interest for detecting and estimating an extent of damage on the surface of interest, and (v) a memory to store instructions on how to process the captured digital image or video for detecting and estimating the damages using computer vision.

One or more images or a video of the damage on the surface of interest may be captured using at least one camera of the portable computing device. To capture an image or video of a damage on the reflective surface, the light source of the portable computing device may be activated and the light emitting from the light source may be directed towards the damage on the surface of interest. Further, a camera feature of the portable computing device may be activated and the at least one camera may be pointed towards the damage on the surface of interest to capture one or more images or video of the damaged surface. Responsively, the processor of the portable computing device may render an image or video feed from the at least one camera sensor on the display of the portable computing device. The image or video feed that is rendered on the display may be pre-processed by the processor of the portable computing device to compensate/account for various camera sensor characteristics, variable lighting conditions (both natural light and artificial light from the light source), and/or desired image properties. Furthermore, the processor of the portable computing device may generate and overlay graphical cues on the image or video feed that is rendered on the display. The graphical cues may be configured to: (i) indicate a preferred/desired positioning of the damage within a captured image (e.g., in the center of the captured image), and/or (ii) guide a user on how to position the at least one camera of the portable computing device to optimize the reflection patterns of the light from the light source (flash) to best highlight the damage in the captured image or video.

Once the at least one camera of the portable computing device is positioned as directed by the graphical cues, one or more images or a video of a portion of the surface of interest that has the damage is captured. In an example where images are captured using the at least one camera, the portable computing device processes the one or more captured images to find one final image that best highlights/depicts the damage on the surface of interest. Alternatively, the portable computing device can combine a subset of the one or more captured images to obtain the final that best highlights/depicts the damage on the surface of interest. In another example where a video is captured using the at least one camera, one or more frames of the video with most optimal reflection pattern for the detection of the damage (highlighting the damage) or one or more images having highest saliency values may be selected by the portable computing device to form a short video, e.g., a short video, an animated Graphics Interchange Format (GIF) image, etc. In some examples, a user may be allowed to select one or more frames of the video that is used for damage detection processing.

When more than one cameras are used for capturing the one or more images or video, the portable computing device may generate a set of images from the one or more images or video for creating an output image that better highlights the damage while providing a stereoscopic effect, i.e., a depth dimension to the highlighted damage.

In addition to receiving the one or more captured images or video, the portable computing device receives a user input that indicates a type of the damage, i.e., whether the damage is a dent or a scratch. Depending on whether the damage is a dent or a scratch, the final image or captured one or more images may be subjected to a dent detection process or a scratch detection process, respectively. Alternatively, the portable computing device may not receive a user input identifying the type of damage. Instead, the final image or the captured one or more images may be subjected to both the dent detection process and the scratch detection process, and the type of damage may be determined based on which one of the two processes has a positive read.

To detect a dent, the portable computing device blurs the final image (with optimal reflection pattern) to remove high frequency edge components. Further, the portable computing device applies a saliency algorithm on the blurred image to generate a single false color image in which less salient (or prominent) features of the blurred image are damped or eliminated and more salient features that exceed a certain threshold are enhanced. For example, in the false color image, the reflections (less salient trait) may be damped/eliminated, while light accumulating in certain spots on the surface as the result of local curvature of the surface, such as in a dent, are enhanced. In other words, since the dent or the border of the dent is a more salient feature, the dent or border of the dent becomes more clear in false colored image, thereby improving the ability to detect the dent within the false color image. Responsive to generating the false color image, the portable computing device presents the false color image on the display of the portable computing device or transmits the false color image to a remote location for presentation, documenting, and/or further analysis.

In the case of a video, i.e., when a video is captured by the at least one camera, the portable computing device blurs the one or more image frames that have been selected from the captured video to form the short video or GIF and applies saliency algorithm on each of the blurred one or more image frames to generate a set of false color images in which less salient (or prominent) features of the blurred image are damped or eliminated and more salient features that exceed a certain threshold are enhanced. Responsively, the portable computing device selects the best false color image and presents the selected false color image on the display of the portable computing device. Alternatively, the portable computing device can provide an option to the user to select one false color image from the set of false color images.

To detect a scratch, the portable computing device determines if the pixel density of images captured by the camera is less than a threshold pixel density. Responsive to a positive determination that the pixel density of the captured images is lesser than the threshold pixel density value, the portable computing device may process the captured images using super-resolution techniques to create a final image with a high pixel density. For example, the portable computing device may superimpose the captured images over each other to generate a final image with an enhanced resolution. If the pixel density of at least one of the one or more captured images is greater than the threshold pixel density value, the portable computing device assigns the at least one image as the final image for further scratch detection processing. In either case, once the final image has been created, based on the color of the finished surface of interest, the portable computing device stretches the color space of the final image to define the edges of the scratch in more detail. Once the color space of the final image has been stretched, the portable computing device analyzes the pixels of the color space stretched image to determine a color gradient. Responsive to determining a color gradient, the portable computing device determines if the pixels representing the color gradient are within a narrow band of pixels and if they are aligned in a line. If the pixels representing the color gradient are within a narrow band of pixels and are aligned in a line, the portable computing device may identify that the pixels represent a scratch. Further, the color space stretched image may be presented on the display of the portable computing device or transmitted to a remote location for presentation, documentation, and/or further analysis.

Similar to dent detection, when a video is captured by the at least one camera, the one or more image frames selected from the captured video to form the short video or GIF is checked for pixel density. Responsive to determining that the pixel density of the image frames are lower than a threshold pixel density value, the portable computing device enhances a resolution of each image frame to create a set of final images by superimposing neighboring image frames of each image frame with the respective image frame. Once the set of final images are created, the portable computing device stretches the color space of each final image, identifies a color gradient in each color space stretched final image, and identifies a deep-scratch as described above. Responsively, the portable computing device selects the best color space stretched image and presents the selected color space stretched image on the display of the portable computing device. Alternatively, the portable computing device can provide an option to the user to select one color space stretched image from the set of color space stretched images.

In addition to detecting the damage, the portable computing device may also be used to determine the size of the damage. In order to determine the size of the damage, a ruler/line gauge is placed adjacent to the damage on the surface of interest. Further, one or more images and/or videos of a portion of the surface of interest with the damage is captured along with the ruler using the camera of the portable computing device. Then, as described above, the portable computing device generates a final image or a set of final images using the one or more captured images and/or videos. Responsive to generating the final image or set of final images, the portable computing device identifies and removes the pixels corresponding to ruler in the final image or the set of final images based on a geometry and/or color of the ruler. Once the pixels corresponding to the ruler are removed, the final image or the set of final images is subjected to the dent detection process and/or the scratch detection process as described above. Then, the pixels corresponding to the ruler are added back to on output of the dent detection process and/or the scratch detection process, e.g., the false color image and/or color space stretched image, to determine a size of the damage on the surface of interest. The portable computing device may present the false color image or color space stretched image comprising the ruler on the display of the portable computing device or transmit it to a remote location for presentation, documentation, and/or further analysis.

In certain example aspects, the portable computing device may automatically determine and provide the size of the damage within a certain confidence interval using the ruler as a reference. The portable computing device may also provide an option to the user to override the automatic size determination feature.

The system, method, and apparatus described in the present disclosure facilitates damage detection and damage size determination in a cost and time efficient manner under variable lighting conditions compared to existing automated damage detection technology that required cost and time-intensive solutions including a pre-set environment with specialized structured lights. Further, the system, method, and apparatus described in the present disclosure provides an improved image processing and analysis technique for accurately detecting and estimating the extent of damage on a reflective surface from an image having considerable amount of reflections.

These and other aspects, features, and embodiments of the disclosure will become apparent to a person of ordinary skill in the art upon consideration of the following brief description of the figures and detailed description of illustrated embodiments.

BRIEF DESCRIPTION OF THE DRAWINGS

The foregoing and other features and aspects of the disclosure are best understood with reference to the following description of certain example embodiments, when read in conjunction with the accompanying drawings, wherein.

Figure 1A:
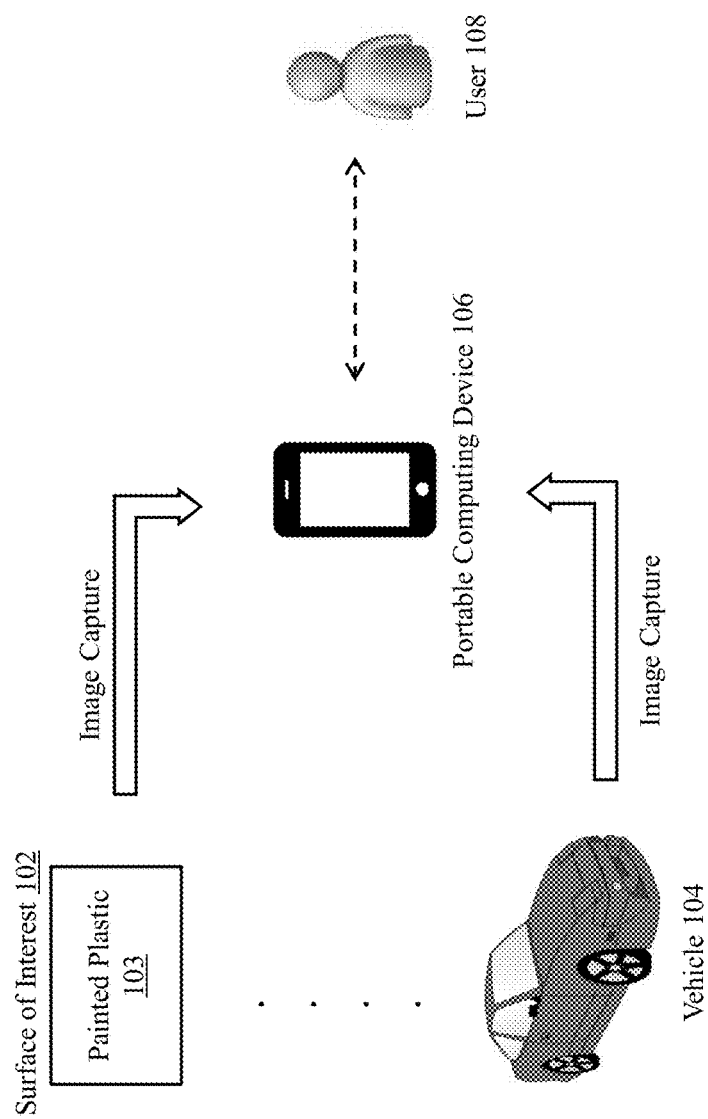
FIG. 1A illustrates an example operating environment of a surface damage detection and sizing system, in accordance with example embodiments of the present disclosure.

The drawings illustrate only example embodiments of the disclosure and are therefore not to be considered limiting of its scope, as the disclosure may admit to other equally effective embodiments. The elements and features shown in the drawings are not necessarily to scale, emphasis instead being placed upon clearly illustrating the principles of the example embodiments. Additionally, certain dimensions or positioning may be exaggerated to help visually convey such principles.

DETAILED DESCRIPTION OF EXAMPLE EMBODIMENTS

In the following paragraphs, a system, method, and apparatus for accurately detecting and estimating an extent of a damage on a reflective surface using an image and/or video of the damage on the reflective surface captured under variable lighting conditions will be described in further detail by way of examples with reference to the attached drawings. In the description, well known components, methods, and/or processing techniques are omitted or are briefly described so as not to obscure the disclosure. As used herein, the "present disclosure" refers to any one of the embodiments of the disclosure described herein and any equivalents. Furthermore, reference to various feature(s) of the "present disclosure" is not to suggest that all embodiments must include the referenced feature(s).

The system, method, and apparatus of the present disclosure is directed towards detecting and estimating the extent of damages on a reflective surface by exposing the reflective surface to light from a light source, capturing images and/or video of the reflective surface that is exposed to light, and processing and analyzing the images (having reflections from the reflective surface) using improved computer vision algorithms to generate an output image that better highlights/depicts the damages on the reflective surface. In one example, a portable computing device, such as a cell phone, smart phone, tablet, etc., equipped with a camera and/or a light source (flash light/assistive light or any other non-structured light source) is used to capture an image and/or video of the reflective surface that is exposed to a light from the light source. If the damage is dent, the image is then processed using a saliency algorithm to better highlight the dents on the reflective surface. Alternatively, if the damage is a scratch, the image is processed using super-resolution, color stretching, and/or other appropriate techniques to better highlight the scratches on the reflective surface. Further, to determine the size and/or orientation of the dent or the scratch, a ruler is placed adjacent to the dent or scratch while capturing the image of the reflective surface that is exposed to the light. The ruler is then removed from the captured image prior to the dent or scratch detection, and added back after detection of the dent or scratch.

The system, method, and apparatus for detecting damages on reflective surfaces will be further described in greater detail below in association with FIGS. 1-12. However, before discussing the example embodiment directed to the system, method, and apparatus for damage detection on a reflective surface, it may assist the reader to understand the various terms used herein by way of a general description of the terms in the following paragraphs.

The term 'reflective surface,' as used herein may generally refer to any appropriate tangible or physical surface that has reflective properties. Example reflective surfaces can include, but are not limited to, metallic surfaces, vehicle body/surfaces, opaque glass, coated furniture, painted metal, painted plastic 103, etc.

The term 'damages on a surface,' as used herein may generally refer to any appropriate flaw on the surface. Example damages can include, but are not limited to, dents, bubbling, cracks, scratches, etc. The term 'deep scratch,' as user herein may generally refer to a scratch that breaks through the depth of a top coat of a surface such that an undercoat of the surface is exposed. For example, in vehicles, a deep scratch may refer to a scratch that breaks through a top coat of paint on the vehicle surface such that a white or matte undercoat on the vehicle surface is exposed.

The term 'portable computing device,' as used herein can include any appropriate hand held computing device, such as, but not limited to, a cell phone, a smartphone, a personal digital assistant, a tablet, a phablet, etc. In certain example embodiments, the portable computing device is equipped with a camera and a flash for capturing an image. However, in other example embodiments, the portable computing device may not include the flash. Instead, other external assistive light may be used to provide lighting on an object whose image is to be captured by the camera. In yet another example embodiment, the portable computing device can be an independent image capture device, such as, a camera or video recorder with an assistive light (flash), a processor to process and analyze the image, a memory, and/or a transceiver for wired or wireless transmission of data.

The term 'image feed,' as used herein generally refers to what is seen by a camera or what the camera is pointing at. For example, in digital cameras with a light sensor, the image feed may refer to an image formed by the combination of light sensed by the sensor of the camera or the image received by the sensor of the camera. The raw image feed may be rendered on a display of the portable computing device or the raw image feed may be pre-processed to compensate/account for lighting conditions, characteristics of the camera sensor, etc., prior to being displayed. In either case, the image feed rendered on the display may operate as a viewfinder that allows a user to compose an image or video prior to capturing the image or recording the video.

The term 'color stretching,' or 'color space stretching,' as used herein generally refers to a technique that enhances the color separation of an image to improve visual interpretation and/or to make feature discrimination easier. In one example, 'color stretching,' or 'color space stretching,' refers to a technique of stretching the primary colors (Red, Green, Blue) or stretching certain properties of the primary colors (e.g., contrast, hue, intensity, etc.) to equalize a color variance of an image. Different tools such as decorrelation stretching, high color ranging, etc., can be used to achieve color stretching or color space stretching.

The term 'super-resolution,' as used herein generally refers to a technique for enhancing the resolution or pixel density of an image. Further, the term 'false color image,' as used herein generally refers to an image that depicts an object in colors that differ from those a photograph (a "true-color" image) would show. In contrast to the true-color image where the colors of an object in the image appear to a human observer the same way as if this observer were to directly view the object, a false-color image sacrifices natural color rendition in order to ease the detection of features in the image that are not readily discernible otherwise.

Technology associated with the system, apparatus, and method for detecting and estimating an extent of a damage on a surface of interest will now be described in greater detail with reference to FIGS. 1-12. In particular, first, FIGS. 1A and 1B (collectively 'FIG. 1') will be discussed in the context of describing representative operating environments associated with the system, method, and apparatus for damage detection and size determination according to certain exemplary embodiments of the present invention. Further, FIGS. 2-12 will be discussed, making exemplary reference back to FIG. 1 as may be appropriate or helpful.

It will be appreciated that the various embodiments discussed herein need not necessarily belong to the same group of exemplary embodiments, and may be grouped into various other embodiments not explicitly disclosed herein. In the following description, for purposes of explanation, numerous specific details are set forth in order to provide a thorough understanding of the various embodiments.

Turning to FIG. 1A, this figure illustrates an example operating environment of a system for detecting and sizing a damage on a reflective surface, in accordance with example embodiments of the present disclosure. In particular, a system 100 includes a surface of interest 102, a portable computing device 106 equipped with an image capture device (e.g., camera 202) (shown in FIGS. 2A and 2B), and a user 108 that interacts with the portable computing device 106 (via a user interface 201 (shown in FIGS. 2A and 2B)) to capture an image of a damage on the surface of interest 102.

As described above, the surface of interest 102 can include any appropriate reflective surface that may be damaged, such as, a painted metal, painted plastic, vehicle body/surface 104, opaque glass, etc. Even though the present disclosure describes detecting and sizing a damage on a reflective surface, one of ordinary skill in the art can understand and appreciate that, in other example embodiments, the system 100 of the present disclosure can be used to detect and size a damage on any other appropriate surfaces, e.g., low-reflective surfaces, as well as show variances of depth on a surface that is not damaged, such as texture or rippling of fabric, decorative panels, objects, etc., without departing from a broader scope of the present disclosure.

In one example embodiment, the surface of interest 102 may have a damage, such as a dent or a deep scratch. To detect and size the damage on the surface of interest 102, the user 108 may interact with a user interface 201 (shown in FIGS. 2A and 2B) of the portable computing device 106 to: (a) illuminate a portion of the surface of interest 102 that is damaged using an assistive light 204 (shown in FIGS. 2A and 2B) of the portable computing device 106, and (b) capture one or more images of the damage on the surface of interest 102 that is illuminated using the assistive light 204. The term 'assistive light source,' as used herein may refer to a camera flash. In some example embodiments, the images of the damage on the surface of interest 102 may be captured without light from the assistive light source 204. In certain example embodiments, instead of the one or more images, a video of the damaged surface of interest may be captured.

The interaction of the user 108 with the portable computing device 106 may include visual interaction, such as, gestures; auditory interaction, such as, voice commands; and/or tactile interaction, such as, touching an appropriate surface of the portable computing device, pressing a key on a keypad of the portable computing device, etc.

Once the image or video of the damage on the surface of interest 102 has been captured, the portable computing device 108 may be configured to process and analyze the captured image or video to generate an output image that better highlights the damage on the surface of interest 102 and/or to determine a size of the damage. Furthermore, the processed/output image that better highlights the damage may be presented to the user 108 via a display 250 (shown in FIGS. 2A and 2B) of the portable computing device 106. In certain example embodiments, the size of the damage may be automatically calculated by the portable computing device 108 and presented to the user 108 within a certain confidence interval. However, in other example embodiments, the processed/output image that is presented to the user 108 may include a ruler that may assist the user to manually determine the size of the damage.

In either case, upon being presented with the processed image, the user 108 may choose to transmit the processed image from the portable computing device 106 to a remote server for documentation of the damage and further analysis. For example, the user 108 may transmit the processed image to a server of a claims management entity for documenting the damage and determine costs associated with the damage.

Figure 1B:
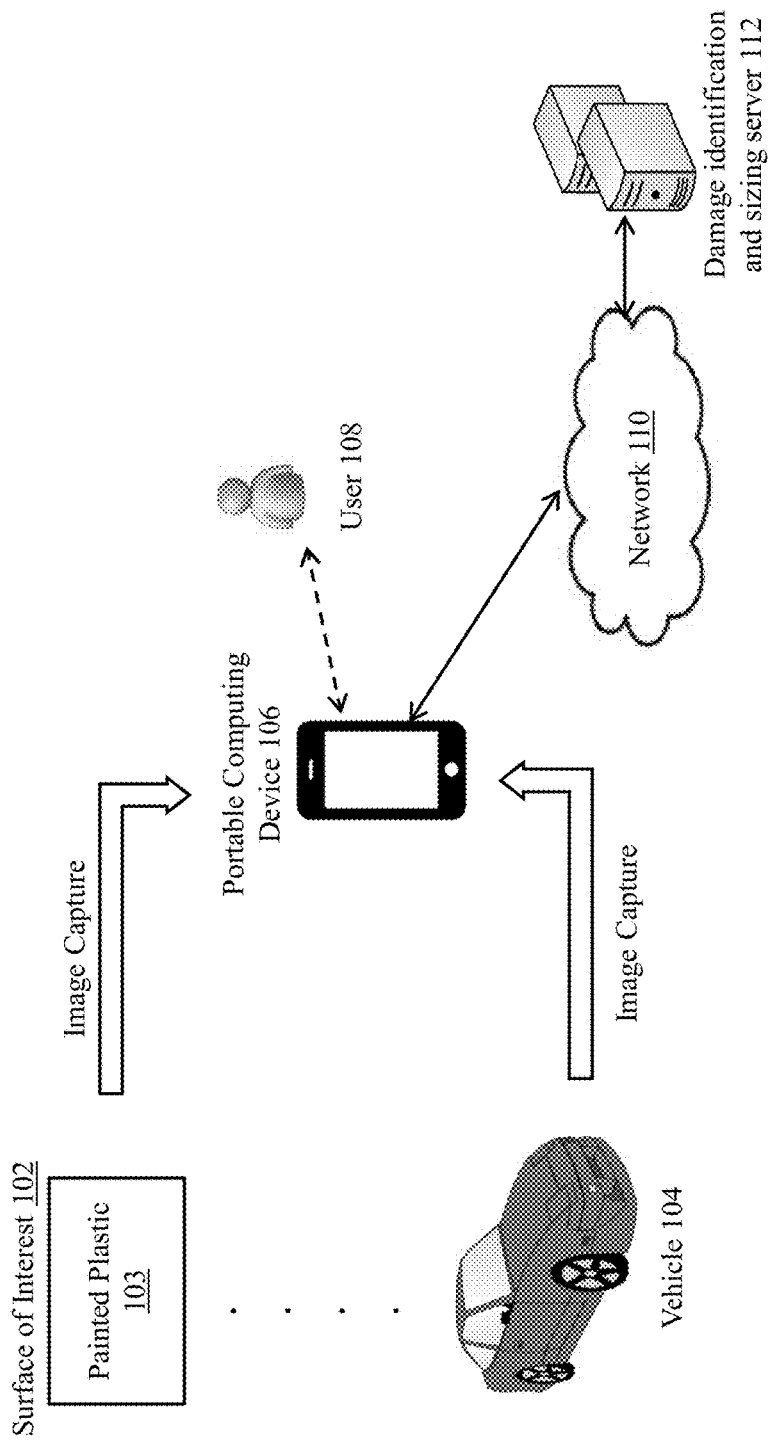
FIG. 1B illustrates another example operating environment of a surface damage detection and sizing system, in accordance with example embodiments of the present disclosure.

Even though FIG. 1A describes that the portable computing device 106 performs the detection and sizing of the damage on the surface of interest, one of ordinary skill in the art can understand and appreciate that, in some example embodiments, e.g., as illustrated in FIG. 1B, the detection and sizing of the damage on the surface of interest 102 may be performed external to the portable computing device 106.

Turning to FIG. 1B, this figure illustrates another example operating environment of a surface damage detection and sizing system, in accordance with example embodiments of the present disclosure. It is noted that FIG. 1B is substantially similar to FIG. 1A, except that one or more of the damage detection and sizing operations may be performed in a damage identification and sizing server 112 that is external to and communicably coupled to the portable computing device 106 via a wired and/or a wireless network 110. In the example embodiment illustrated in FIG. 1B, the user 108 may interact with the portable computing device 106 to capture one or more images or video of the damage on the surface of interest 102. However, instead of processing the one or more images or video at the portable computing device 106 for detecting and sizing the damage as described in FIG. 1A, in the example embodiment of FIG. 1B, the portable computing device 106 may transmit the captured images (or a final image) to the damage identification and sizing server 112 (herein 'server 112') via the wired and/or wireless network 110. Responsive to receiving the captured images (or the final image), the server 112 may process and analyze the images or video to detect and size the damage on the surface of interest.

In said example embodiment illustrated in FIG. 1B, a client instance of the server 112 may be downloaded on the portable computing device 106 to guide a user to capture the image or video of the damage on the surface of interest 102 such that the reflection patterns of the flash are optimized to best highlight the damage, e.g., by using graphical cues. By transferring the image processing and analysis operations to the server 112, the system 200 of FIG. 1B releases the resources and processing power of the portable computing device for execution of other applications on the portable computing device. In certain example embodiments, the captured images may be transmitted to the server 112 as and when the images are captured by the portable computing device 106. However, in other example embodiments, the captured images or video may be transmitted to the server 112 after a predetermined time interval or after a predetermined number of images have been captured, e.g., as batch data.

In either case, once the server 112 processes and analyzes the images or video to generate an output image that better highlights the damage on the surface of interest 102, the server 112 may transmit the processed/output image back to the portable computing device 106 for presentation to the user 108 via the display 250 of the portable computing device. The processed/output image may include a ruler to assist a user in manually determining the size of the damage. Alternatively, in addition to the processed/output image, the server 112 may transmit a size of the damage for presentation via the display 250 of the portable computing device 106. In some example embodiments, the server 112 may transmit an alert message to the portable computing device 106 that informs the user 108 that the captured image has been processed and analyzed to detect and estimate an extent of the damage. The alert message may include a web link that the user 108 can select via the user interface 201 of the portable computing device 106. The web link provides the user 108 access to the processed image stored in the server 112. The portable computing device 106 and the server 112 will be further described below in greater detail in association with FIGS. 2A and 2B.

Figure 2A:
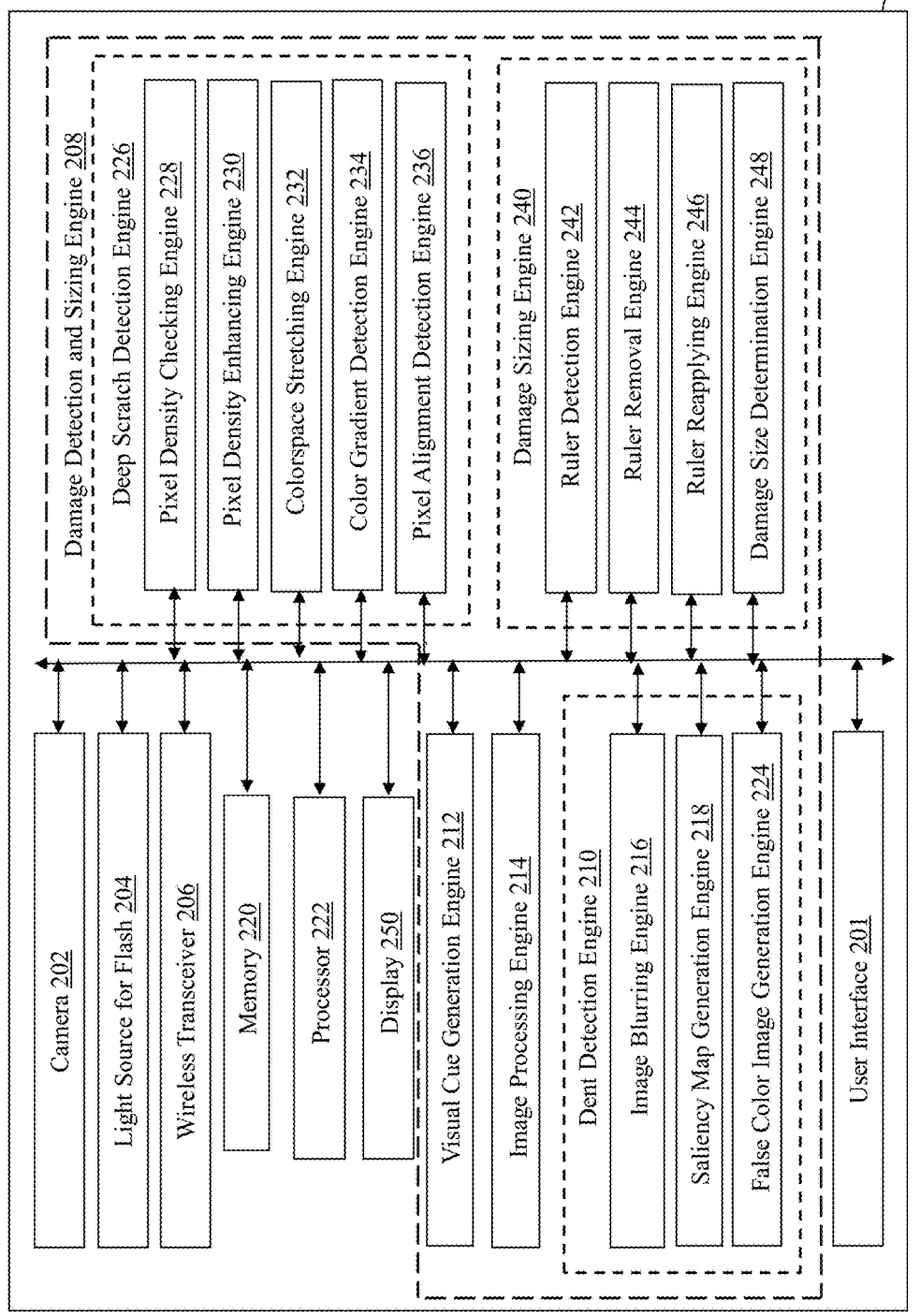
FIG. 2A illustrates a block diagram of the portable computing device of FIG. 1A with a damage detection and sizing engine, in accordance with example embodiments of the present disclosure.

Turning to FIG. 2A, this figure illustrates a block diagram of the portable computing device of FIG. 1A, in accordance with example embodiments of the present disclosure. In particular, the portable computing device 106 includes a user interface 201, a camera 202, an assistive light source 204, a wireless transceiver 206, a memory 220, a processor 222, a display 250, and a damage detection and sizing engine 208.

The processor 222 of the portable computing device 106 may be a multi-core processor or a combination of multiple single core processors. Further, the portable computing device 106 may include a memory 220 that is coupled to the processor 222. The memory 220 may be non-transitory storage medium, in one embodiment, and a transitory storage medium in another embodiment. The memory 220 may include instructions that may be executed by the processor 222 to perform operations of the portable computing device 106, e.g., capturing an image, detecting and estimating an extent of a damage on a surface of interest 102 using the image, etc. In other words, operations associated with the different engines 210-218 and 224-248, the camera 202, the assistive light source 204, the wireless transceiver 206, and the user interface 201 of the portable computing device 106 may be executed using the processor 222.

The wireless transceiver 206 of the portable computing device 106 may be configured to enable communication to and from the portable computing device 106. Further, as described above, the user interface 201 may be configured to receive a user input from a user 108 through a visual interaction, a auditory interaction, and/or a tactile interaction. Accordingly, the user interface 201 may include, but is not limited to, a touchscreen, a keypad, a microphone, a motion capture device, the camera 202, etc. In certain example embodiments, the display 250 and/or the camera 202 of the portable computing device 106 may operate as a user interface 201. For example, the display 250 may be a touchscreen display that the user 108 can interact with to capture an image, to zoom in/zoom out a captured image, and/or for other interactive operations.

The camera 202 may be configured to capture an image or video of an object or area of interest to the user 108. Even though FIGS. 2A (and 2B) illustrates a camera 202, one of ordinary skill in the art can understand and appreciate that, in other example embodiments, a video recording device may be used in addition to or instead of the camera 202 without departing from a broader scope of the present disclosure. That is, the camera 202 may be replaced by any other appropriate image capturing device without departing from a broader scope of the present disclosure. Additionally, even though the present disclosure describes the portable computing device 106 as having one camera 202, one of ordinary skill in the art can understand and appreciate that in other example embodiments, the portable computing device 106 can include more than one camera, each of which may capture an image or video of the object or area of interest without departing from a broader scope of the present disclosure. For example, the portable computing device 106 may have two cameras that mimic a left eye and right eye effect.

Further, as illustrated in FIGS. 2A (and 2B) the portable computing device 106 may include an assistive light source 204 that operates as a flash which provides additional artificial lighting while capturing an image using the camera 202. That is, the assistive light source 204 may be configured to generate light that is used to illuminate an object or area of which an image or video is to be captured. The assistive light source 204 may be a light emitting diode (LED). However, in other example embodiments, the assistive light source 204 may be any other appropriate point or non-point light source without departing from a broader scope of the present disclosure. Although FIGS. 2A (and 2B) of the present disclosure illustrates an assistive light source 204 as being part of the portable computing device 106, one of ordinary skill in the art can understand and appreciate that, in other example embodiments, the assistive light source 204 may be external to the portable computing device 106.

The display 250 of the portable computing device 106 may be configured to visually present an image as seen by the camera 202 and/or a processed/output image that better highlights the damage on the surface of interest 102. Additionally, as described above, the display 250 may be used to interact with one or more features of the portable computing device 106.

To detect and estimate an extent of a damage on a surface of interest 102, initially, the user 106 may activate the assistive light source 204 and the camera 204 of the portable computing device 106 via the user interface 201. Then, the user 108 may point the camera 202 and the assistive light source 204 of the portable computing device 106 towards the portion of the surface of interest 102 that is damaged. Light from the assistive light source 204 may illuminate the portion of the surface of interest 102 that is damaged. In certain example embodiments, based on the external lighting conditions (natural light availability), the portable computing device 106 may override the activation of the assistive light source 204 by the user 106. That is, if the portable computing device 106 determines that an appropriate amount of the natural light or other external light is available, the flash may be de-activated.

Once the camera is activated and pointed towards the portion of the surface of interest 102 that is damaged, the processor 222 of the portable computing device 106 may contemporaneously render an image feed of the camera 202 on the display 250 of the portable computing device 106, thereby allowing the user 108 to see the input received by the camera 202. Since the camera 202 is pointed towards the damage on the surface of interest, the image feed of the camera 202 that is rendered on the display 250 may be an image of the portion of the surface of interest 102 that is damaged. As described above, the image feed of the camera 202 that is rendered on the display 250 may be pre-processed by the processor 222 of the portable computing device 106 to compensate/account for the characteristics of the camera, the variable lighting conditions, etc.

In addition to rendering the image feed of the camera 202 on the display 250, the processor 222 may interact with the visual cue generation engine 212 (a sub component of the damage detection and sizing engine 208) to generate one or more graphical cues to assist/guide a user 108 on how to position the camera 202 for optimizing the reflection patterns of the light from the assistive light source 204 to best highlight the damage within the rendered image feed. The visual cue generation engine 212 may create and overlay one or more graphical cues on the image feed that is rendered on the display 250. The one or more graphical cues as described herein may include, but are not limited to, cross-hairs, boxes, arrows, etc. Further, in addition to the graphical cues that assist/guide a user 108 to obtain an image that best highlights the damage on the surface of interest 102, the visual cue generation engine 212 may provide other graphical cues that prompts the user 108 to capture the image when camera 202 is at the apt position for capturing the image that best highlights the damage is available. Even though the present disclosure describes visual cues being used to guide a user 108 to capture an image that best highlights the damage on the surface of interest, one of ordinary skill in the art can understand and appreciate that in other example embodiments, other type of cues, such as, auditory or tactile cues may be provided without departing from a broader scope of the present disclosure.

In either case, once the camera 202 position is finalized, the user 108 may interact with the user interface 201 to capture, using the camera 202, one or multiple images or videos of the portion of the surface of interest 102 that has the damage (herein 'damaged surface). In certain example embodiments, the camera 202 may capture a single image using the current intensity of light from the assistive light source (herein 'flash'), while, in other example embodiments, the processor 222 of the portable computing device 106 may operate in unison with the camera 202 to modulate the light intensity of the flash and capture multiple images at different light intensities of the flash. In other example embodiments, the multiple images may be captured at a constant light intensity of the flash. In yet another example embodiment, one or more of the multiple images may be captured without a flash. It is noted that even though multiple images are captured by the camera 202, it may appear to a user as if only one image is being captured. That is, even though the user 108 clicks once to capture an image, the camera 202 may be capturing multiple images. Further, in other example embodiments, a video of the damaged surface of interest may be captured.

Responsive to capturing the images or video, the image processing engine 214 may determine whether the one or more captured images or selected image frames (for video) should be transmitted to the dent detection engine 210 or the deep scratch detection engine 226. Said determination may be made based a user input that identifies a type of the damage. The user input identifying the type of the damage may be provided by a user 108 in response to a query generated by the processor 222 either prior to capturing the image or after capturing the image. The query requests the user to enter a type of the damage. Alternatively, in some embodiments, the image processing engine 214 may transmit the one or more captured images or selected image frames to both the dent detection engine 210 and the deep scratch detection engine 226 which may process the final image in parallel. In said embodiment, the image processing engine 214 may determine the type of damage based on which of the two engines, dent detection engine 210 and the deep scratch detection engine 226, provides a positive damage detection read. For example, if the deep scratch detection engine 226 provides a positive read, the image processing engine 214 may determine that the damage is a deep-scratch. Similarly, if the dent detection engine 210 provides a positive read, the image processing engine 214 may determine that the damage is a dent.

When the image processing engine 214 identifies the damage as being a dent based on a user input, the image processing engine 214 may transmit the final image to the dent detection engine 210 that is configured to transform the final image into a false color image that better highlights the dent. Upon receiving the final image, the image processing engine 214 may assign the one captured image as a final captured image (herein 'final image') for further damage detection processing. However, when the image processing engine 214 receives multiple captured images, the image processing engine 214 may process the multiple captured images to identify one image of the multiple captured images that best depicts the damage on the surface of interest 102 (herein 'damage'). The identified one image may be assigned as the final image. The one image may be identified based on a reflection pattern in the image. In other words, the image processing engine 214 may assign an image that has the most optimal reflection for damage detection as the final image. Alternatively, the image processing engine 214 may combine one or more of the multiple captured images to create the final image that best depicts the damage. In case of a video, the image processing engine 214 may be configured to generate a short video of GIF from the captured video. In other example, the image processing engine 214 may be configured to select one or more image frames from the video based on a saliency value of the images frames. In yet another example, the image processing engine 214 may operate in concert with the user interface 201 and the display 250 to provide an option to a user 108 to select the one or more image frames from the video.

Once the final image or the one or more image frames is created, the image processing engine 214 forwards the final image to the image blurring engine 216 that blurs the final image by removing high frequency edge components of the final image. The final image may be blurred to smoothen the final image and to remove tiny salient features, such as, reflections from tiny specks in the paint of a vehicle body (provided the surface of interest is a vehicle body), grains from camera sensor noise, etc., thereby ensuring that a saliency algorithm that is applied on the blurred image focuses on salient features that are above a threshold size, such as a dent on the surface of interest.

Responsive to blurring the final image, the image blurring engine 216 forwards the blurred image to the saliency map generation engine 218. The saliency map generation engine 218 may apply a saliency algorithm on the blurred image to identify salient features in the blurred image. In particular, the saliency map generation engine 218 may process the blurred image to generate a saliency map which is a set of values that indicate the saliency of each pixel of the blurred image. Further, the saliency map generation engine 218 may normalize the saliency map by normalizing the set of values that indicate the saliency of each pixel. Thresholds may be applied to adjust the saliency map, for instance to minimize false positives and improve the detection of the dents that exceed certain size or typology or to normalize the final image. For example, pixels having a saliency value above a threshold saliency value may be deleted or damped and the other pixels may be enhanced. Once the saliency map has been normalized, the saliency map generation engine 218 may transmit the normalized saliency map to the false color image generation engine 224 to create a false color image that better highlights the damage on the surface of interest 102. The false color image generation engine 224 may multiply the blurred image with the normalized saliency map to generate the false color image in which less salient features such as reflections are damped and more salient features such as dents (or borders of dents) are enhanced. In other words, multiplying the values of the normalized saliency map with corresponding pixels of the blurred image results in a false color image, e.g., a grayscale image, heat-map image, etc., in which the dent on the surface of interest is more prominently displayed (better highlighted for easy detection).

For a video, the image blurring engine 216, the saliency map generation engine 218, and/or the false color image generation engine 224 may operate in concert to process each of the one or more image frames to generate a set of false color images as described above. Further, either the dent detection engine or a user selects the best false color image for presentation via the display 250.

If the image processing engine 214 identifies the damage as a deep-scratch based on a user input, the image processing engine 214 may transmits the one or more images captured by the camera to the deep scratch detection engine 226. Responsive to receiving the one or more captured images, the deep scratch detection engine 226 may forward the one or more captured images to the pixel density checking engine 228 that determines the pixel density of the one or more captured images and compares the pixel density of the one or more captured images with a threshold pixel density. If the pixel density of the one or more images is lesser than the threshold pixel density, the pixel density checking engine 228 may operate in unison with the pixel density enhancing engine 230 to create a final image having a higher pixel density (resolution). In particular, the pixel density enhancing engine 230 may superimpose the one or more captured images to create the final image having a higher pixel density.

Once the pixel density of final image is determined to be greater than a threshold pixel density, the pixel density enhancing engine 230 transmits the final image to the colorspace stretching engine 232 that stretches a colorspace of the final image to define the edge of a damage, which in this case is a deep-scratch, in more detail. Responsive to stretching the colorspace of the final image, the color gradient detection engine 234 performs a pixel by pixel analysis of the colorspace stretched image to identify a color gradient between the pixels of the colorspace stretched image. Upon identifying a color gradient, the color gradient detection engine 234 determines if the pixels corresponding to the color gradient are within a narrow band of pixels. If the pixels corresponding to the color gradient are within a narrow band of pixels, the color gradient detection engine 234 operates in concert with the pixel alignment detection engine 236 to determine if the pixels corresponding to the color gradient are aligned along a line (preferably continuous). If the pixels representing the color gradient are aligned along a line, the deep scratch detection engine 226 may identify the pixels as representing a deep scratch on the surface of interest 102. Further, in some example embodiments, the pixel alignment detection engine 236 may record a start pixel and an end pixel of the pixels representing the deep scratch for determining a size (e.g., length) of the deep scratch. However, if the pixels representing the color gradient are not within a narrow band of pixels and/or if they are not aligned in a line, the deep scratch detection engine 226 may identify the pixels as a false spot, i.e., not a deep scratch.

Similar to the dent detection process, in the case of a video, pixel density checking engine 228, the colorspace stretching engine 232, color gradient detection engine 234, and/or the pixel alignment detection engine 236 may operate in concert to process each of the selected one or more image frames of the video and generate a set of colorspace stretched images. Further, either the deep scratch detection engine or a user selects the best colorspace stretched image for presentation via the display 250.

In addition to the dent detection engine 210 and the deep scratch detection engine 226, the damage detection and sizing engine 208 may include a damage sizing engine 240 that is configured to automatically determine the size of a damage on the surface of interest or assist the user 108 to manually determine the size of the damage on the surface of interest. To determine the size of the damage, the user 108 may have to capture one or multiple images or video of the damage with a ruler placed adjacent to the damage. Responsive to capturing the images or the video of damage with the ruler placed adjacent to the damage, the image processing engine 214 may generate a final image (or set of final images in case of a video) as described above. The final image may include the damage and ruler that is placed adjacent to the damage. Further, the image processing engine 214 may transmit the final image to the damage sizing engine 240 which in turn forwards the final image to the ruler detection engine 242. Upon receiving the final image with the damage and the ruler, the ruler detection engine 242 may determine the pixels in the final image (or set of final images in case of a video) that correspond to the ruler based on a geometry and/or a color of the ruler. Further, the ruler detection engine 242 operates in concert with the ruler removal engine 244 to remove the ruler from the image (or set of final images in case of a video) by cutting out pixels that correspond to the ruler. The ruler is removed because the ruler may be a more salient feature than the damage and therefore, the ruler may interfere with detection on the damage that may be less salient than the ruler.

Responsive to removing the ruler from the final image (or set of final images in case of a video), the damage sizing engine 240 may transmit the final image (or set of final images in case of a video) to the image processing server 214 which in turn transmits the final image to the dent detection engine 210 and/or the deep scratch detection engine 226 for detecting a dent or a deep scratch as described above. Once the false color image or the colorspace stretched image that better highlights the dent or the deep scratch, respectively, has been generated dent detection engine 210 and/or the deep scratch detection engine 226, said images may be transmitted back to the damage sizing engine 240 which in turn transmits said images to the ruler reapplying engine 246. In particular, the ruler reapplying engine 246 may add the cut-out pixels that correspond to the ruler into the false color image or the colorspace stretched image. Additionally, the damage size determination engine 248 may automatically determine the size of the dent or deep scratch using the ruler as a reference. In one example embodiment, to determine the size of the deep scratch, the damage size determination engine 248 may use the ruler in combination with the start and end pixels of the deep scratch that is determined by the pixel alignment detection engine 236.

Responsive to generating the false color image, the colorspace stretched image, and/or determining the size of the damage; the dent detection engine 210, the deep scratch detection engine 226, and/or the damage sizing engine 240 may operate in concert with the processor 222 and the display 250 to present the false color image, the colorspace stretched image, and/or the size of the damage to the user 108. In certain example embodiments, the portable computing device 106 may provide the user 108 an option to override the automatic size determination feature. In either case, once the false color image, the colorspace stretched image, and/or size of the damage is presented to the user 108, the user 108 may transmit, via the wireless transceiver 206, the presented images and/or size information to a remote server, such as a claims management entity server for documentation and/or further analysis.

Figure 2B:
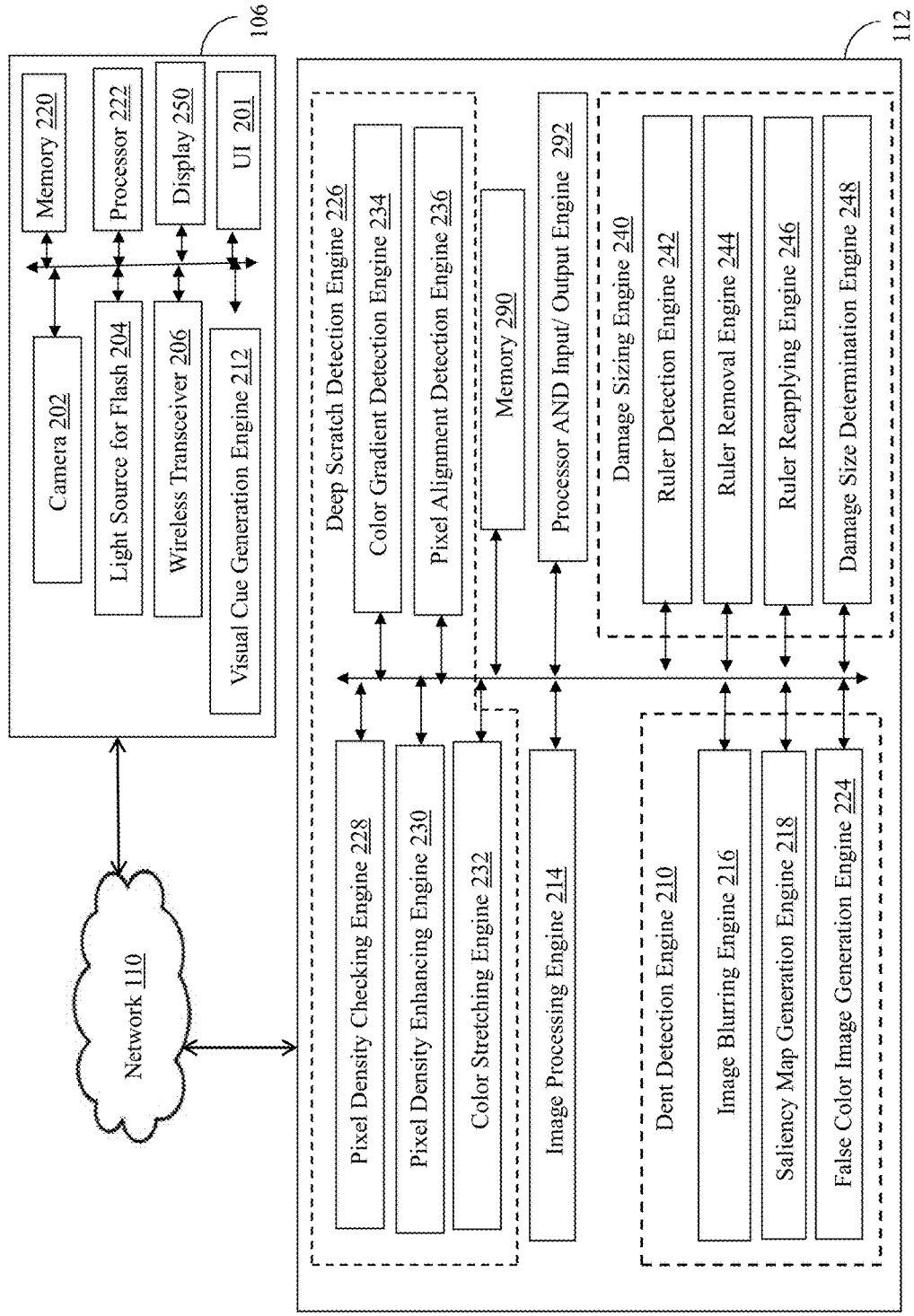
FIG. 2B illustrates a block diagram of the portable computing device and the damage detection and sizing server of FIG. 1B, in accordance with example embodiments of the present disclosure.

Even though FIG. 2A illustrates the damage detection and sizing engine 208 as being disposed in the portable computing device 106, one of ordinary skill in the art can understand and appreciate that in other example embodiments, the damage detection and sizing engine may be implemented external to the portable computing device 106, such as, in a server 112 as illustrated in FIG. 2B. Turning to FIG. 2B, this figure illustrates a block diagram of the portable computing device and the damage detection and sizing server of FIG. 1B, in accordance with example embodiments of the present disclosure. At the onset, it is noted that FIG. 2B may be substantially similar to FIG. 2A, except that one or more components of the dent detection and sizing engine 208 is implemented in server 112 that is communicably coupled to the portable computing device 106 via the network 110. As described above in association with FIG. 1B, the portable computing device 106 of FIG. 2B may be configured to capture one or multiple images of the damage or a damage along with a ruler. Responsive to capturing the images, the portable computing device 106 may transmit the captured one or multiple images to the server 112 that is configured to detect and size the damage using the damage detection and sizing engine 208. The transmitted images may be received by the input/output engine 292 of the server 112 and forwarded to the image processing engine 214. In addition to receiving the images from the portable computing device 106, the input/output engine 292 may be configured to transmit the false color image, the colorspace stretched image, and/or the size of the damage outputted by the engines 210, 214-218, and 224-248 of the server 112 to the portable computing device 106 for presentation to the user 108 via the display 250 of the portable computing device 106. The operations of the engines 210, 214-218, and 224-248 are described above in association with FIG. 2A and will not be repeated herein for the sake of brevity. Further, the memory 290 of the server 112 may include instructions that may be executed by the processor 292 to perform operations of the engines 210, 214-218, and 224-248. Similarly, the memory 220 of the portable computing device 106 may include instructions that may be executed by the processor 222 to perform operations of the portable computing device 106.

Even though FIG. 2B illustrates engines 210, 214-218, and 224-248 of the damage detection and sizing engine 208 being implemented in the server 112, one of ordinary skill in the art can understand appreciate that, in other example embodiments, one or more of said engines may be implemented in the portable computing device 106. For example, in some embodiments, the image processing engine 214 may be implemented in the portable computing device 106. Accordingly, in addition to capturing one or multiple images of the damaged surface, the portable computing device may also process the one or multiple images to generate a final image. In said example embodiment, the portable computing device 106 may transmit the final image to the server 112 for further processing, i.e., damage detection and sizing.

Turning now to FIGS. 3-12, these figures include flow charts that illustrate the process for detecting and sizing a damage on a surface of interest using images of the damage captured using a portable computing device. Although specific operations are disclosed in the flowcharts illustrated in FIGS. 3-12, such operations are exemplary. That is, embodiments of the present invention are well suited to performing various other operations or variations of the operations recited in the flowcharts. It is appreciated that the operations in the flowcharts illustrated in FIGS. 3-12 may be performed in an order different than presented, and that not all of the operations in the flowcharts may be performed.

All, or a portion of, the embodiments described by the flowcharts illustrated in FIGS. 3-12 can be implemented using computer-readable and computer-executable instructions which reside, for example, in computer-usable media of a computer system or like device. As described above, certain processes and operations of the present invention are realized, in one embodiment, as a series of instructions (e.g., software programs) that reside within computer readable memory of a computer system and are executed by the processor of the computer system. When executed, the instructions cause the computer system to implement the functionality of the present invention as described below.

Figure 3:
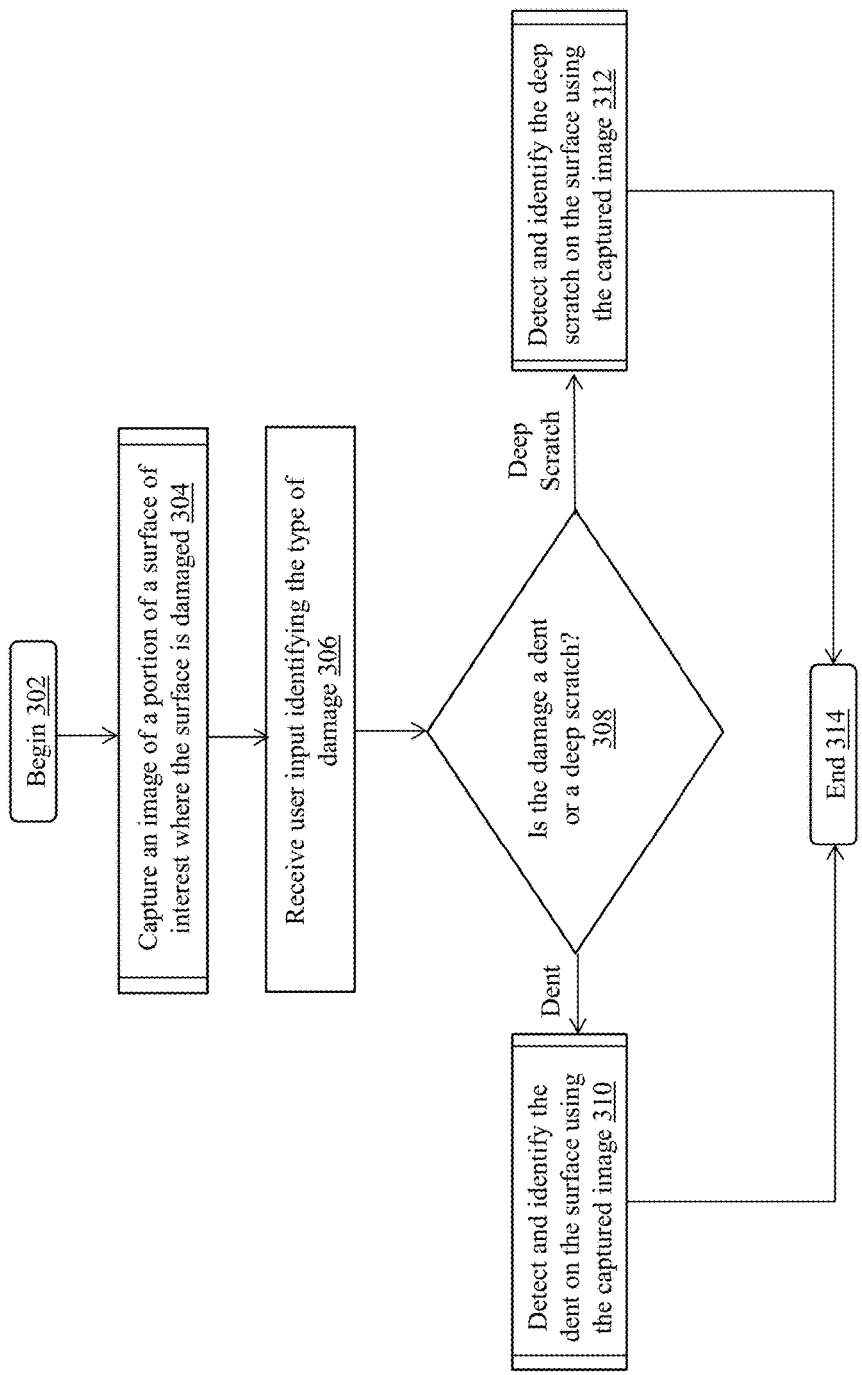
FIG. 3 illustrates an example damage detection operation of the damage detection and sizing system illustrated in FIG. 1A, in accordance with example embodiments of the present disclosure.

Turning to FIG. 3, this figure illustrates an example damage detection operation of the damage detection and sizing system illustrated in FIG. 1A, in accordance with example embodiments of the present disclosure. The damage detection process begins at operation 302 and proceeds to operation 304 where one or multiple images of a damaged surface 102 is captured by a user 108 using a camera 202 of the portable computing device 106. Operation 304 will be described in greater detail below, in association with FIG. 5.

Figure 5:
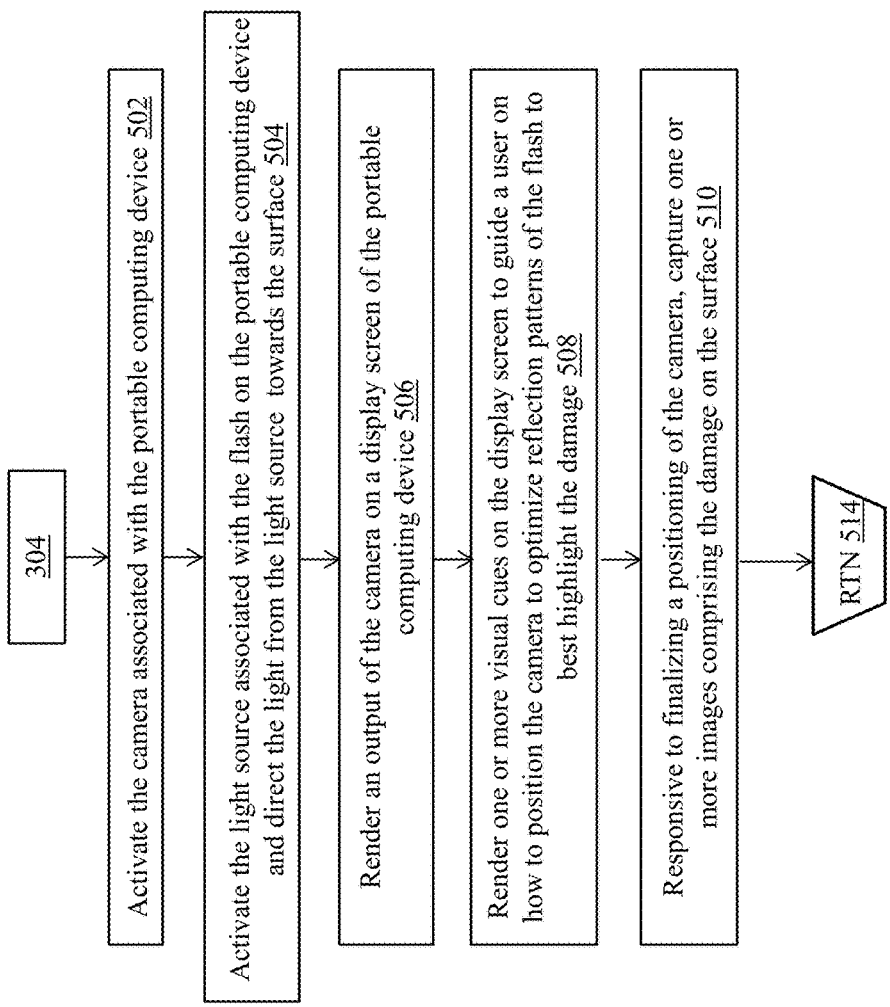
FIG. 5 illustrates an image capture operation of the damage detection operation, in accordance with example embodiments of the present disclosure.

Turning to FIG. 5, this figure illustrates an image capture operation of the damage detection operation, in accordance with example embodiments of the present disclosure. The user 108 may position the camera 202 such that it faces the damaged surface 102 for capturing one or more images of the damaged surface 102. Then, in operation 502, the user 108 may activate camera 202 of the portable computing device 106. Further, in operation 504, the user may activate the flash 204 based on the lighting conditions (natural light and other external artificial light) and direct the light from the flash 204 towards the damaged surface 102. In certain example embodiments, the user 108 may choose not to activate the flash 204 if the external lighting conditions are satisfactory for capturing the image of the damaged surface 102. In other example embodiments, the processor 222 of the portable computing device 106 may automatically determine that the external lighting conditions are satisfactory for capturing an image of the damaged surface 102 and may accordingly, deactivate the flash 204.

In either case, once the camera 202 is activated, in operation 506, the processor 222 of the portable computing device 106 may render an image feed of the camera 202 on the display 250 of the portable computing device 106. In addition to rendering the image feed of the camera 202 on the display 250, in operation 508, the visual cue generation engine 212 may generate and overlay one or more graphical cues on the image feed of the camera 202 that is rendered on the display 250. In certain example embodiments, the visual cue generation engine 212 may generate and overlay two graphical cues—a first visual cue that indicates to a user 108 how and where the damage should be positioned within the image (e.g., center of the image), and a second visual cue that guides a user on how to position the camera 202 to optimize reflected light (of the flash 204) from the damaged surface 102 to best highlight the damage. However, in other example embodiments, lesser or more number of visual cues, auditory cues, or tactile cues may be provided to the user 108 without departing from a broader scope of the present disclosure.

Responsive to finalizing a position of the camera 202 based on the visual cues, the user 108 may provide a signal to the camera 202 via the user interface 201 for capturing the image of the damaged surface. Accordingly, in operation 510, the camera 202 of the portable computing device 106 captures one or multiple images of the damaged surface at different intensities of the flash 204, without the flash 204, and/or at constant intensity of the flash 204.

Responsive to capturing the one or more images, the portable computing device 106 returns to operation 306 of FIG. 3. Turning back to FIG. 3, in operation 306, the portable computing device 106 may receive a user input identifying the type of damage. For example, the user may provide user input identifying the damage as a dent or a deep scratch. Responsive to receiving the user input, in operation 308, the image processing engine 214 of the portable computing device 106 may determine whether the damage is a dent or a deep scratch based on the user input.

If the damage is a dent, the image processing engine 214 proceeds to operation 310 where the final image is transmitted to the dent detection engine 210 for transforming the final image to a false color image that better highlights the dent on the surface of interest 102. Operation 310 will be described in greater detail below, in association with FIG. 8.

Figure 8:
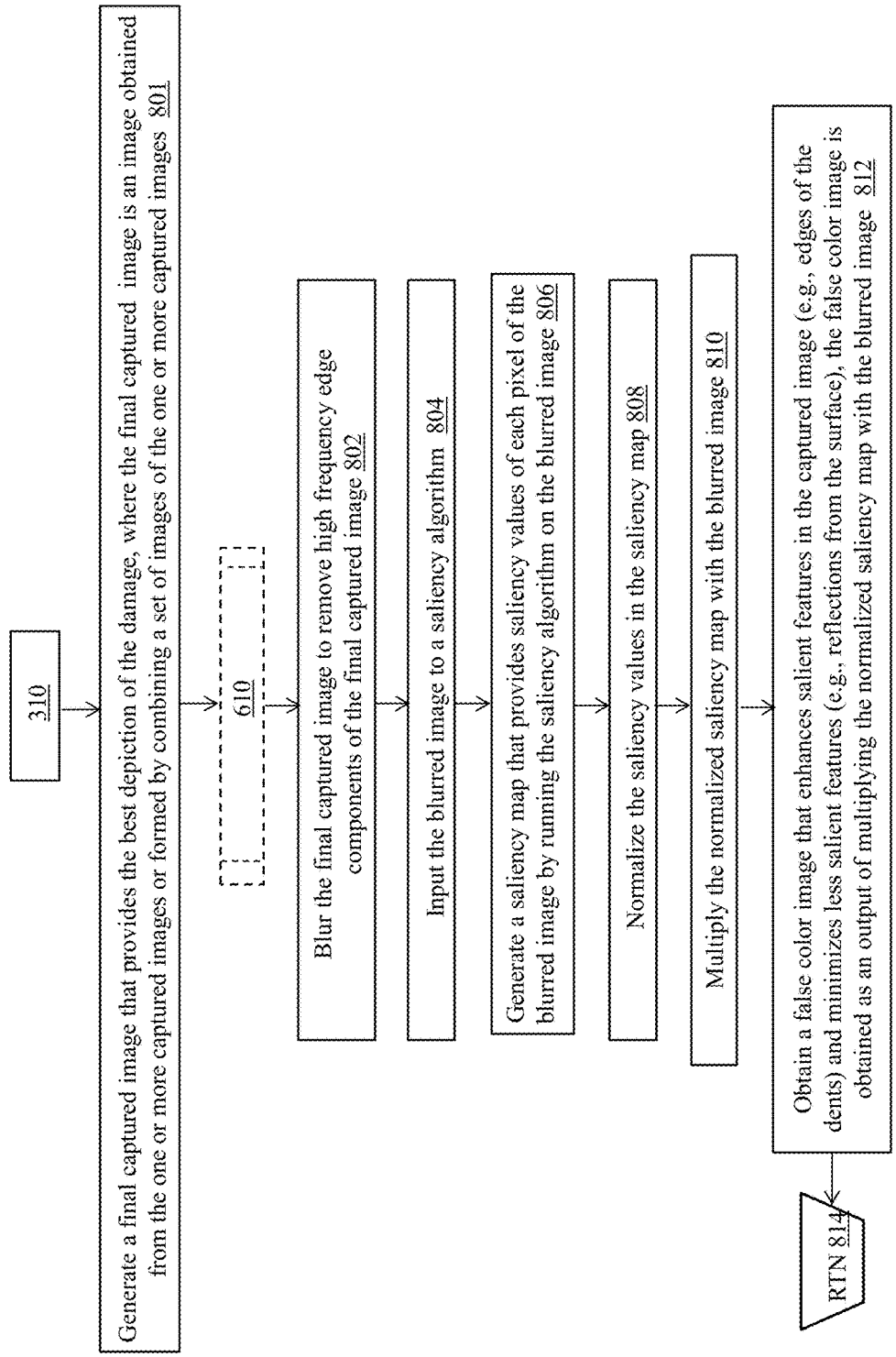
FIG. 8 illustrates a dent detection operation of the damage detection and sizing system, in accordance with example embodiments of the present disclosure.

Turning to FIG. 8, this figure illustrates a dent detection operation of the damage detection and sizing system, in accordance with example embodiments of the present disclosure. Responsive to receiving the one or more captured images, in operation 801, the image processing engine 214 of the portable computing device 106 either generates a final image using the one or multiple captured images of the damaged surface. If only one image is captured, then the one image may be assigned as the final image. When multiple images of the damaged surface are captured, the image processing engine 214 may select one of the images that has the most optimal reflection as the final image. Alternatively, the image processing engine 214 may combine one or more of the multiple images to create the final image. If the image processing engine 214 is unable to generate a final image from the one or multiple captures images, then, the image processing engine 214 may operate in concert with the processor 222 and the visual cue generation engine 212 to generate a message requesting the user 108 to reposition the camera 202 and repeat operation 510 of capturing the one or multiple images.

Figure 13:
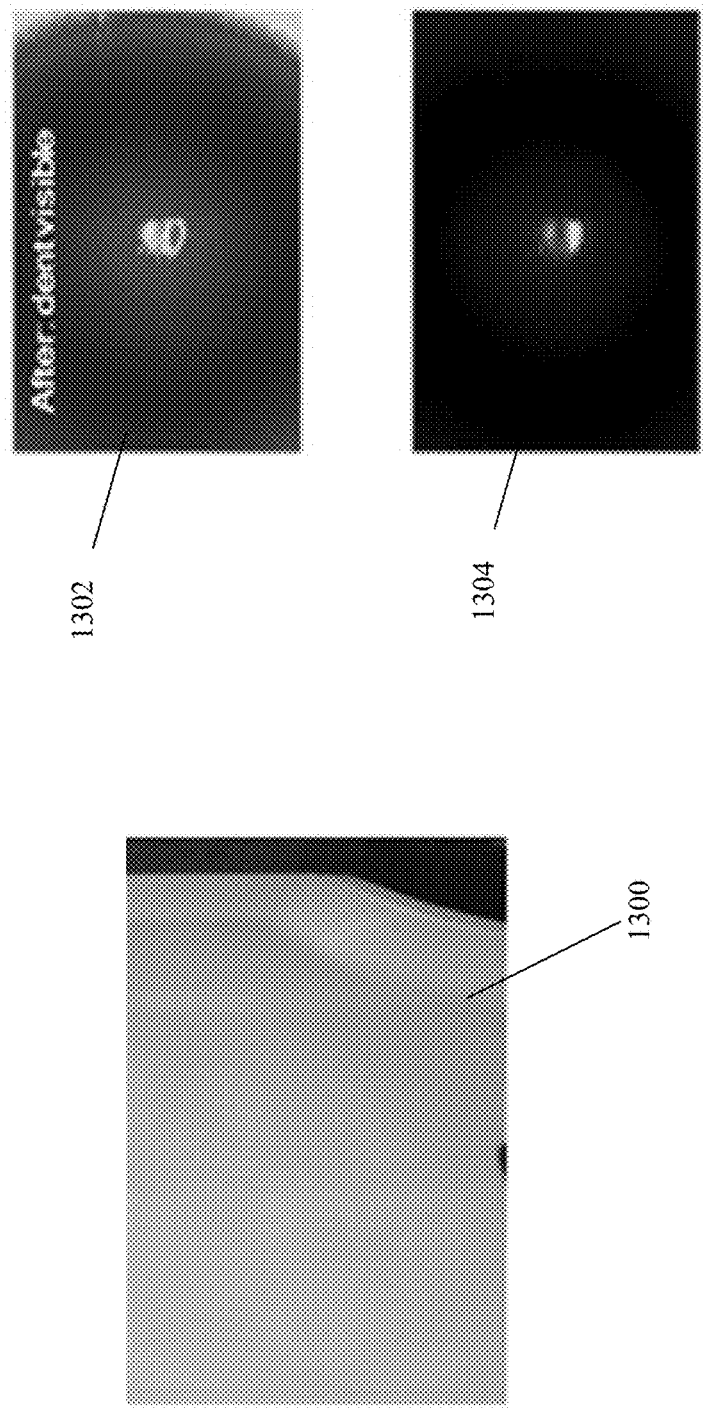
FIG. 13 illustrates an example final image and example false color images that better highlights a dent on a surface of interest, in accordance with example embodiments of the present disclosure.

It is noted that even though the final image may have optimal reflection from the surface of interest 102, in most cases the damage on the surface of interest 102 may still be nearly invisible for various reasons, such as, but not limited to, a small size of the damage, the color of the surface of interest that may blend with the damage, etc. An example final image 1300 is illustrated in FIG. 13 where it is nearly impossible to identify the damage prior to transforming the image to better highlight the damage using the damage detection process.

Responsive to creating the final image, the portable computing device 106 may proceed to operation 610 for removing a ruler from the final image for detecting a size of the damage. It is noted that operation 610 may be omitted if the image of the damage is not captured with the ruler for determining the size of the damage. Operation 610 may be described in greater detail below in association with FIG. 7.

Figure 7:
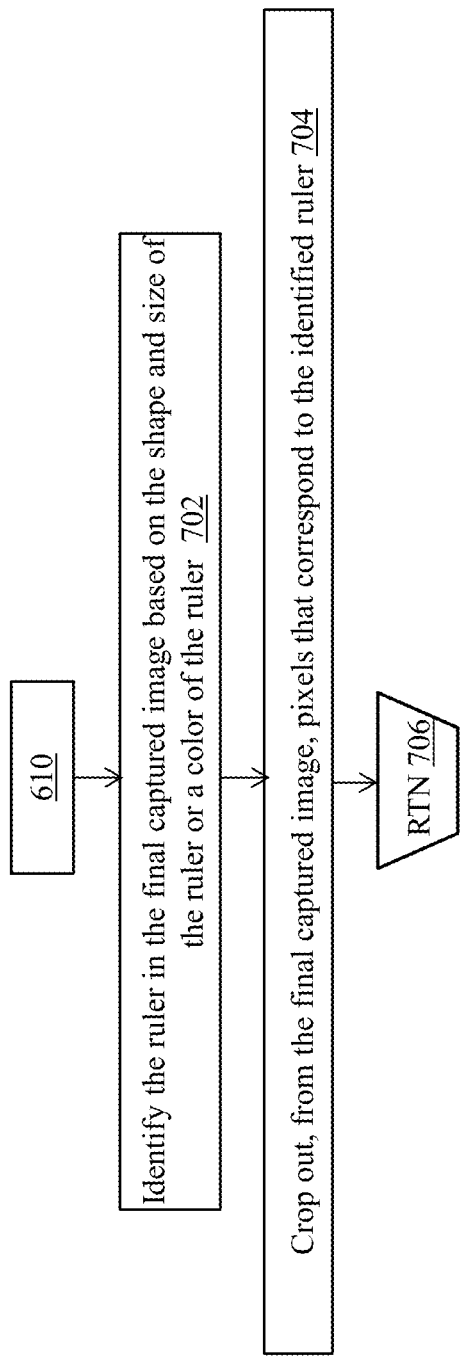
FIG. 7 illustrates a ruler removal operation of the damage detection and sizing system, in accordance with example embodiments of the present disclosure.

Turning to FIG. 7, this figure illustrates a ruler removal operation of the damage detection and sizing system, in accordance with example embodiments of the present disclosure. It is noted that the ruler may be removed from the final image because the ruler may be a more salient feature than the damage. Accordingly, the presence of the ruler in the final image may cause the dent detection process 310 and/or the deep scratch detection process 312 to focus on the ruler rather than on the damage, thereby resulting in a false color image or colorspace stretched image that better highlights the ruler than the damage.

Responsive to receiving the final image, in operation 702, the ruler detection engine 242 may identify the pixels of the final image that correspond to the image of ruler based on a geometry and/or a color of the ruler. For example, the ruler detection engine 242 may identify a shape and/or color in the final image that matches the specific shape and/or color of the ruler. Responsive to identifying the pixels that that correspond to the image of ruler, in operation 704, the ruler removal engine 244 may remove the ruler from the final image by cropping/cutting-out the pixels corresponding to the ruler from the final image. In some example embodiments, in addition to cutting out the pixels that correspond to the ruler, in operation 704, the ruler removal engine 244 may identify a color of the damaged surface and fill the cut-out portion in the final image with pixels having the color of the damaged surface. In either case, responsive to removing the ruler from the final image, the process returns to operation 802 of FIG. 8.

Turning to FIG. 8, in operation 802, the image blurring engine 216 smoothens the final image and removes salient features in the final image that are below a threshold size by removing high frequency edge components of the final image. Then, in operations 804 and 806, the saliency map generation engine 218 receives the blurred image and inputs the blurred image to a saliency algorithm that generates a saliency map as an output. The saliency map comprises saliency values of each pixel of the blurred image. Further, in operation 808, the saliency map generation engine 218 may normalize the saliency values in the saliency map. Then, in operations 810 and 812, the false color image generation engine 224 multiplies the thresholded and normalized saliency map with the blurred image to generate a false color image in which the less salient features (e.g., reflections) are damped and more salient features (e.g., borders of dents, and curves in surface due to dent where light collects, etc.) are enhanced. In other words, the normalized saliency values are applied as weights to corresponding pixels of the blurred image to generate the false color image that better highlights the dent.

The saliency algorithm generates a hierarchical list of features in the blurred image that are arranged based on saliency of each feature. Further, the less salient features of the blurred image are damped and the more salient features of the blurred image are enhanced resulting in a false color image that better highlights the dent.

Example false color images 1302 and 1304 are illustrated in FIG. 13. By comparing the final image 1300 to the false color images 1302 and 1304, it can be seen that the dent that is nearly invisible in the final image 1300 is clearly visible (better highlighted) in the false color images 1302 and 1304 that is generated by processing the final image 1300 using the dent detection operation 310.

Once the false color image is generated, the portable computing device 106 returns to operation 314 in FIG. 3, where the false color image is presented to the user 108 via the display 250 and the process ends. Alternatively, in some embodiments, the final image may include more than one type of damage and accordingly, the process may return to operation 308, where the image processing engine 214 determines if the additional damage in the final image is a deep scratch.

In operation 308, if the image processing engine 214 determines that the damage (or the additional damage) in the final image is a deep scratch, the image processing engine 214 proceeds to operation 312 where the final image is transmitted to the deep scratch detection engine 226 for transforming the final image to a colorspace stretched image that better highlights the deep scratch on the surface of interest 102. Operation 312 will be described below in greater detail, in association with FIG. 9.

Figure 9A:
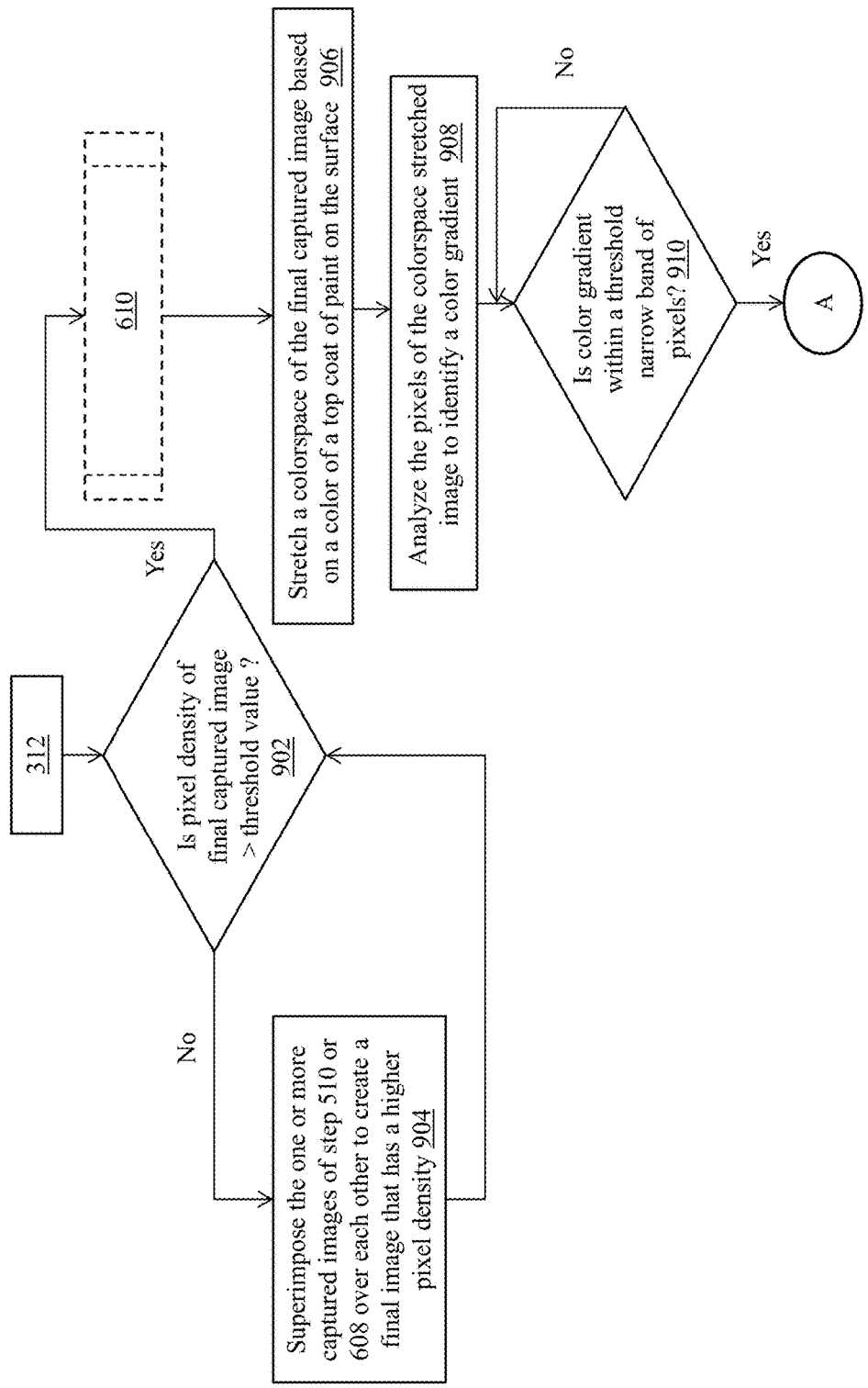
FIGS. 9A and 9B (collectively 'FIG. 9') illustrate a deep scratch detection operation of the damage detection and sizing system, in accordance with example embodiments of the present disclosure.
Figure 9B:
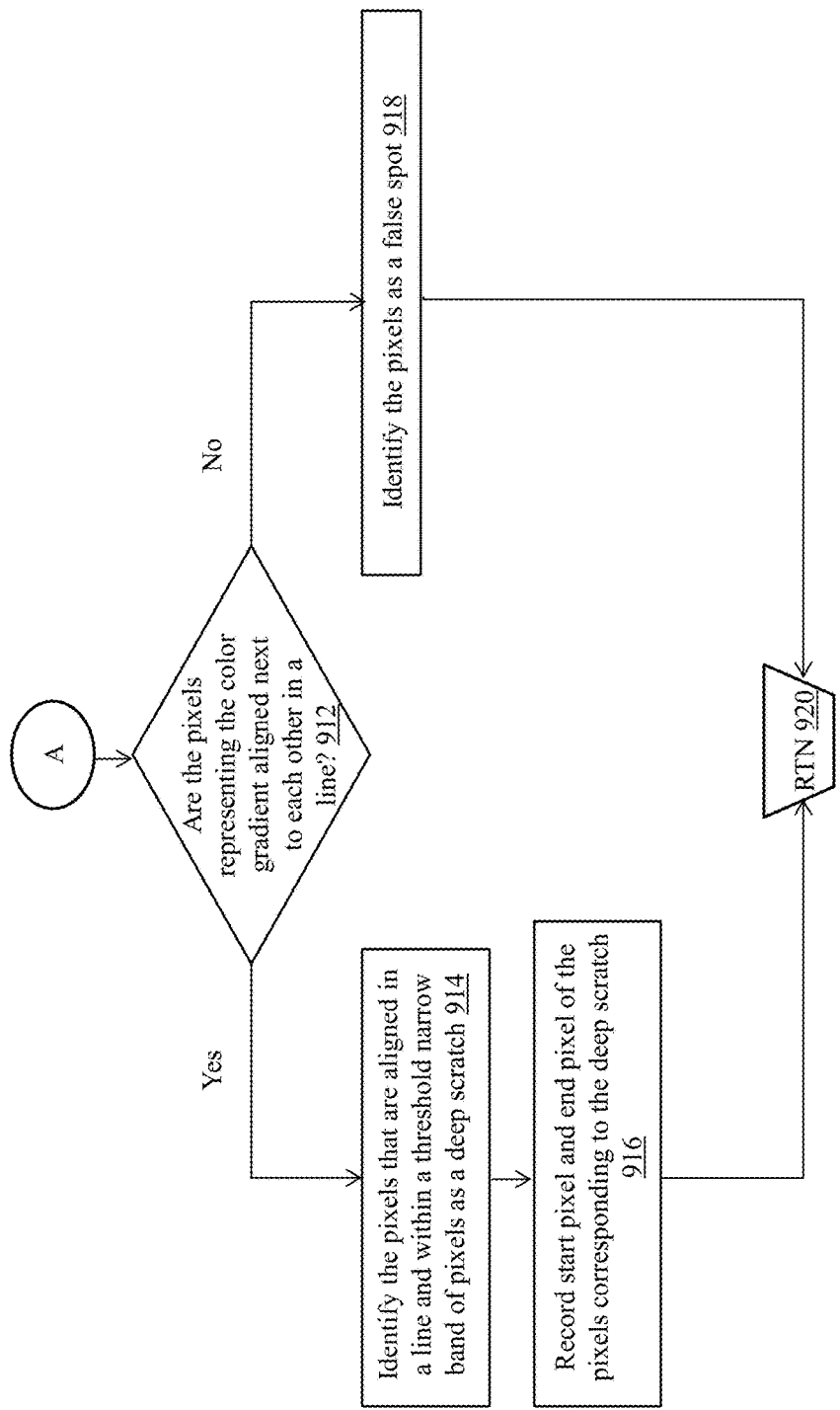
Figure 14:
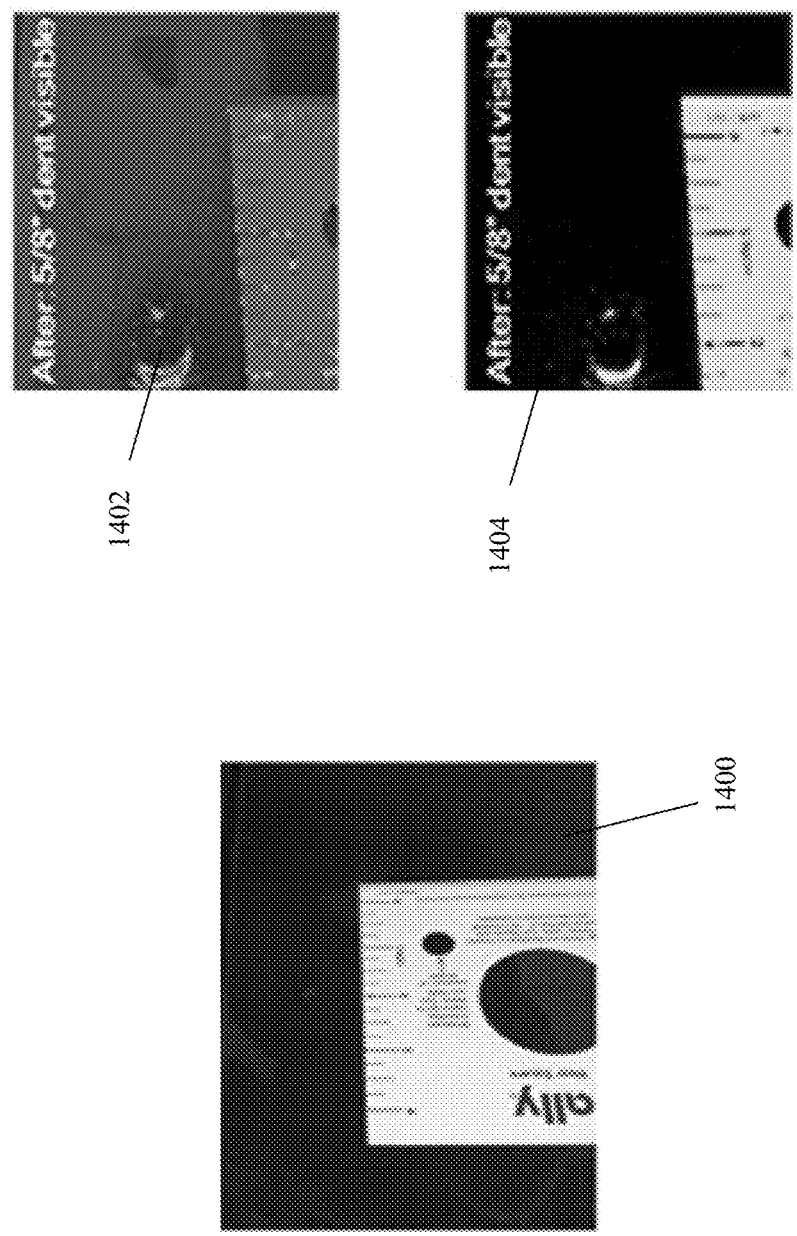
FIG. 14 illustrates an example final image with a ruler and example false color images with the ruler to determine a size of a dent on a surface of interest, in accordance with example embodiments of the present disclosure.

Turning to FIG. 9, this figure illustrates a deep scratch detection operation of the damage detection and sizing system, in accordance with example embodiments of the present disclosure. Responsive to receiving the one or more captured images from operation 510 (or 608 as described later in association with FIG. 6), in operation 902, the pixel density checking engine 228 determines if the pixel density of the one or more captured images is greater than a threshold pixel density value. If the pixel density of the captured images is lesser than the threshold pixel density value, then, in operation 904, the pixel density enhancing engine 230 may combine (superimpose) one or more captured images to create a final image having an enhanced pixel density. An example final image 1400 of a damage with the ruler placed adjacent to the damage is illustrated in FIG. 14. In the example final image 1400, the damage is nearly invisible and further, it is not possible to determine the size of the damage.

Figure 4:
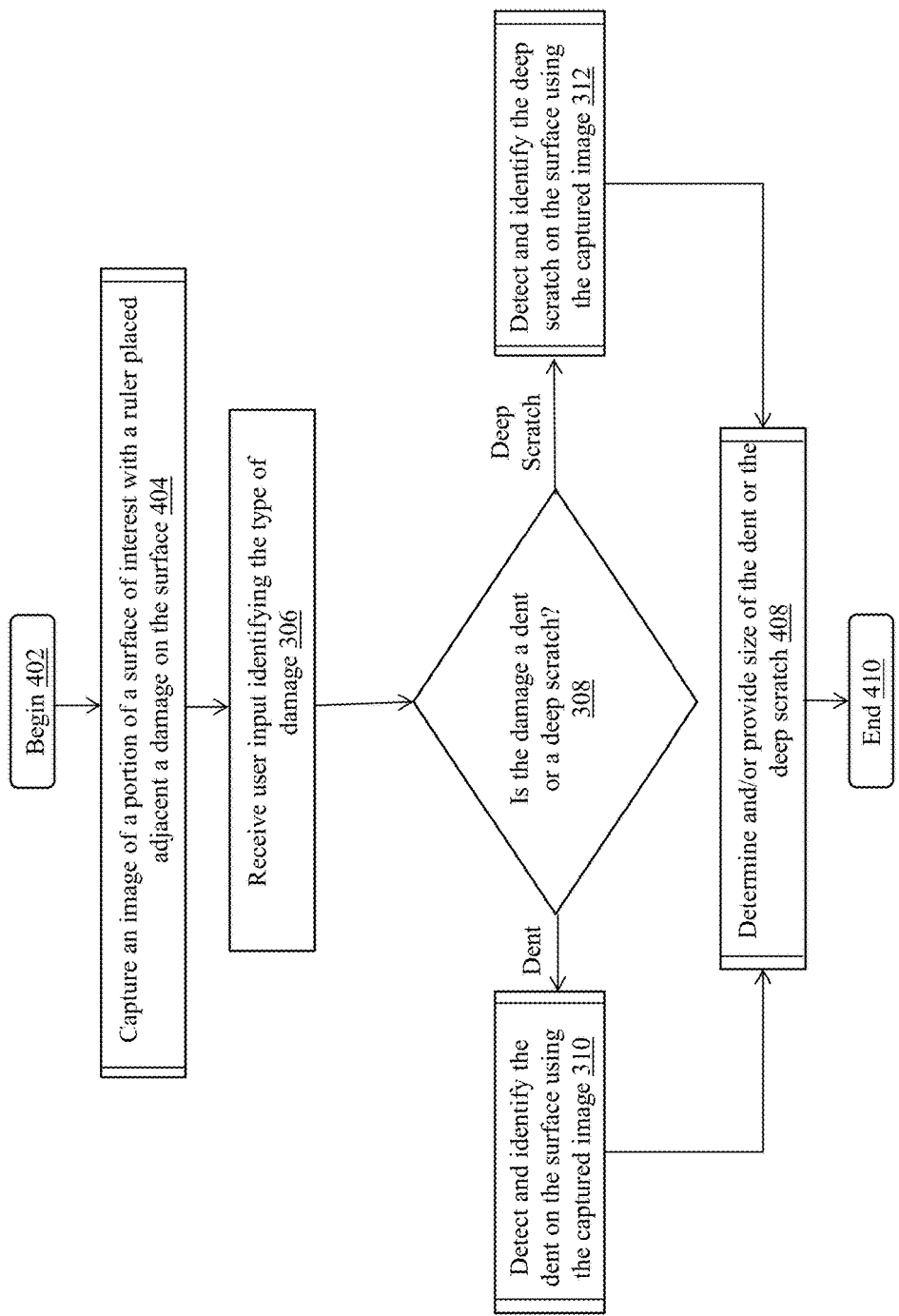
FIG. 4 illustrates an example damage detection and sizing operation of the damage detection and sizing system illustrated in FIG. 1A, in accordance with example embodiments of the present disclosure.

If the pixel density of the final image is greater than the threshold pixel density value or responsive to creating the final image, in operation 610, pixels corresponding to a ruler may be removed from the final image provided the one or more images have been captured with a ruler for size detection. It is noted that, in some example embodiments where size of not being detected (i.e., when images are captured without the ruler as in operation 304), the operation 610 may be omitted. In other words, operation 610 is only included when detection and size estimation of the damage is performed as shown in FIG. 4.

In operation 906, the colorspace stretching engine 232 stretches a colorspace of the final image based on color of the surface of interest 102 to define and edge of the deep scratch in more detail. In particular, the colorspace of the final image may be stretched using various algorithms, such as, decorrelation stretching algorithm, high color ranging algorithm, etc., that modifies the primary colors (R, G, B) or other properties of the primary colors to equalize a color variance of the final image (average the color of the pixels in an area of interest on the image). For example, when the surface of interest 102 is the surface of a vehicle, the colorspace of the final image comprising the deep scratch on the vehicle surface may be stretched based on a top coat of paint on the vehicle surface. That is, if the vehicle top paint is red, then the colorspace of the final image may be stretched such that red color (R plane) is enhanced while the other primary colors (G plane and B plane) are suppressed.

Responsive to stretching the colorspace of the final image, in operation 908, the color gradient detection engine 234 analyzes the colorspace stretched image pixel-by-pixel to identify a color gradient. For example, a portion of the image that represents the deep scratch may have a color gradient. Continuing with the above-mentioned vehicle example, the vehicle may have a top paint that is red and an undercoat that is white. Alternatively, the vehicle may have reflective top coat and a matte finish as the undercoat. In the first example where the vehicle has a red top coat and a white undercoat, the pixels across the deep scratch would have color gradient, i.e., red top coat to white undercoat and back to red top coat. Similarly, in the second example, the color gradient may appear from a difference in reflection pattern from the top reflective coat to the matte undercoat.

Once the color gradient is identified, in operation 910, the color gradient detection engine 234 determines whether the pixels corresponding to the color gradient are within a threshold narrow band of pixels. Responsive to determining that the pixels corresponding to the color gradient are within the threshold narrow band of pixels, in operation 912, the pixel alignment detection engine 236 determines if the pixels corresponding to the color gradient are aligned in a line. If the pixels corresponding to the color gradient are within a threshold narrow band of pixels and are aligned in a line, in operation 914, the deep scratch detection engine 226 identifies that the pixels corresponding to the color gradient represent a deep scratch. Further, in operation 916, the pixel alignment detection engine 236 of the deep scratch detection engine 226 records a start pixel coordinate and end pixel coordinate of the deep scratch for further use in determining the size (length) of the deep scratch.

However, if the pixels corresponding to the color gradient are not within a threshold narrow band of pixels and/or are not aligned in a line, in operation 918, the deep scratch detection engine 226 identifies the pixels as a false spot, i.e., not representing a deep scratch. Responsively, the deep scratch detection engine 226 returns to operation 314 in FIG. 3, where the colorspace stretched image that better highlights the deep scratch is presented to the user 108 via the display 250 and the process ends.

Responsive to presenting the false color image and/or the colorspace stretched image on the display 250, the user 108 may choose to save the image or forward the image to a remote server, such as claims management server for documenting the damages and/or further analysis.

Even though FIG. 3 illustrates operation 306 where the portable computing device receives a user input identifying the type of a damage, in other example embodiments, operation 306 may be omitted and instead, the final image may be subjected to both the dent detection operation 310 and the deep scratch detection operation 312 without departing from a broader scope of the present disclosure. In said example embodiment, the portable computing device 106 determines that type of damage based on which of the two operations, i.e., the dent detection operation 310 or the deep scratch detection operation 312, provides a positive read.

Further, even though the present disclosure describes generating the final image in operation 512, one of ordinary skill in the art can understand and appreciate that in some example embodiments, operation 512 may be omitted without departing from a broader scope of the present disclosure. That is, in said example embodiments, the final image may not be created. Instead, the one or multiple captured images may be directly provided as input to the dent detection engine 210 and/or the deep scratch detection engine 226. The dent detection engine 210 and/or the deep scratch detection engine 226 may generate a false color image and/or a colorspace stretched image, respectively, using the one or multiple captured images. However, the quality of the false color image and/or a colorspace stretched image, i.e., the clarity of the highlighted damage may vary in said images when compared to a false color image and/or a colorspace stretched image that is generated from a final image.

FIG. 3 illustrates a process of better highlighting a damage on a surface of interest. However, in some embodiments, in addition to better highlighting the damage, the user 108 may wish to determine a size of the damage as well. FIG. 4 illustrates an example damage detection and sizing operation of the damage detection and sizing system illustrated in FIG. 1A, in accordance with example embodiments of the present disclosure. Turning to FIG. 4, in operation 404, the user 108 captures an image of the damaged surface along with a ruler that is placed adjacent the damage using the portable computing device 106 associated with the user 108. Operation 404 will be described below in greater detail, in association with FIG. 6.

Figure 6:
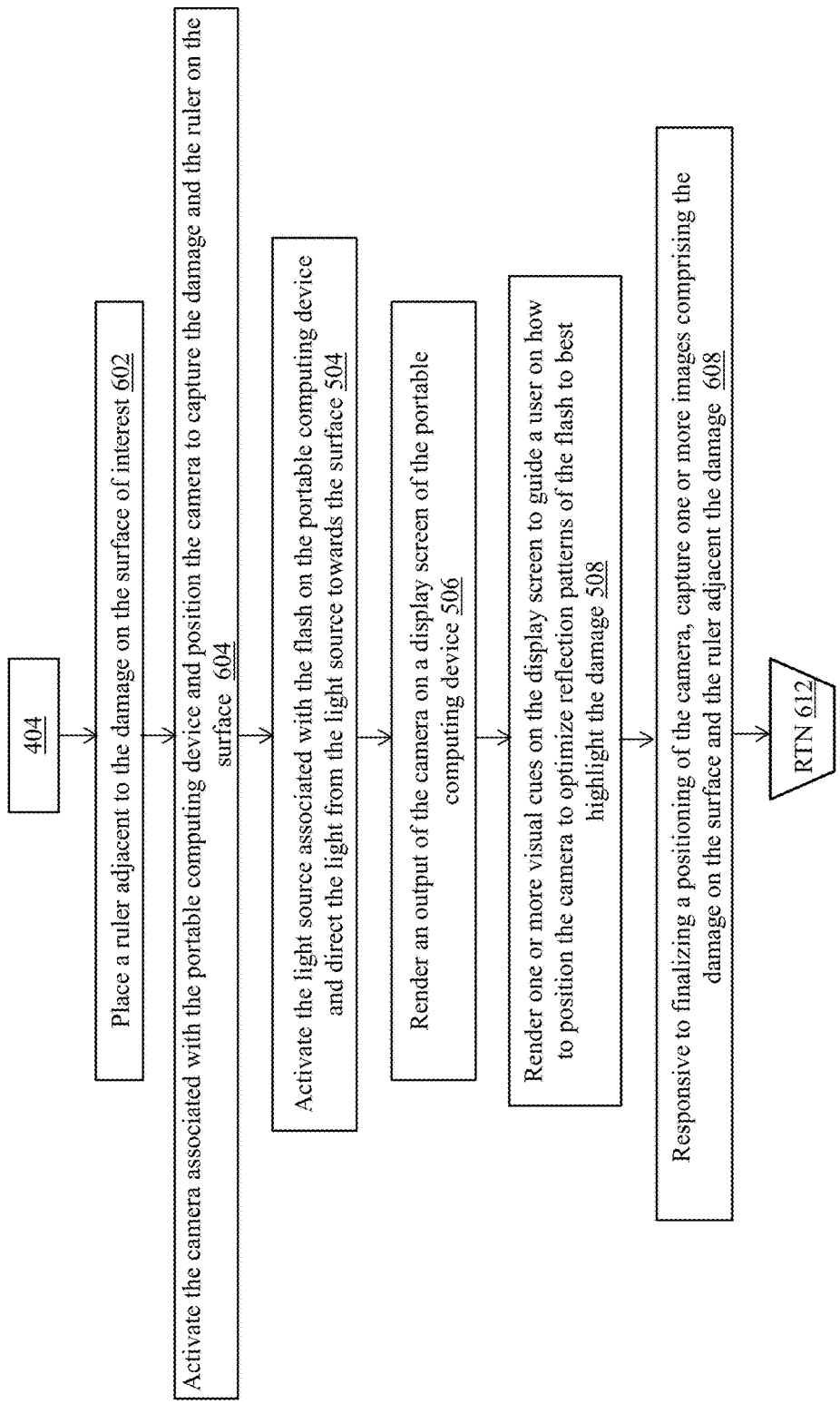
FIG. 6 illustrates an image capture operation of the damage detection and sizing operation, in accordance with example embodiments of the present disclosure.

Turning to FIG. 6, this figure illustrates an image capture operation of the damage detection and sizing operation, in accordance with example embodiments of the present disclosure. In certain example embodiments, the portable computing device 106 may be configured to automatically generate instructions, graphical cues, and/or messages to guide a user 108 on how to use a ruler, where to place the ruler, how to place the ruler adjacent the damage, and/or how to capture an image comprising the damage and the ruler. The instructions and the cues may be generated based on a user's response to a query by the portable computing device on whether the user 108 wants to determine a size of the damage. In other example embodiments, such instructions may be manually downloaded to the portable computing device 106 by the user 108. In either case, based on the instructions and cues, in operation 602, the user 108 may place the ruler (or any other appropriate size measuring device) adjacent the damage on the surface of interest 102.

Further, in operation 604, the user 108 may activate the camera on the portable computing device 106 and position the camera 202 such that an image of the damage and the ruler can be captured. Then, in operation 504, the user 108 may also activate the flash 204 and direct the light from the flash towards the damaged surface. In operation 506, the image feed of the camera 202 may be rendered on a display 250 of the portable computing device. Since the camera is pointed towards the damage and the ruler, the image feed that is rendered on the display 250 may include the damaged surface and the ruler that is placed adjacent the damage. Operations 504 and 506 have been described in greater detail above in association with FIG. 5 and will not be repeated herein for the sake of brevity.

In addition to rendering the image feed of the camera, in operation 508, the visual cue generation engine 212 may generate and overlay one or more visual cues on the rendered image feed to guide a user 108 on how to capture an image of the damaged surface and the ruler that is placed adjacent to the damage. Operation is described in greater detail in association with FIG. 5 and accordingly will not be repeated herein for the sake of brevity. Responsive to finalizing the position of the camera 202, in operation 608, one or multiple images of the damaged surface along with the ruler may be captured using the camera 202 as described above in association with FIG. 5. Once the one or more images are captured, the portable computing device may return to operation 306 of FIG. 4.

Returning to FIG. 4, in operations 306 and 308, the image processing engine 214 may determine whether the final image should sent to the dent detection process 310 or the deep scratch detection process 312 based on the user input received in operation 306. Alternatively, in some example embodiments, operation 306 may be omitted and the final image may be subjected to both the dent detection process 310 and the deep scratch detection process 312 as described above in association with FIG. 3. The dent detection process 310 and the deep scratch detection process 312 have been described above in greater detail in association with FIG. 3. Accordingly, the operations 310 and 312 will not be repeated herein for the sake of brevity. As described above in association with FIG. 3, the dent detection process 310 may transform the final image to a false color image and the deep scratch detection process 312 may transform the final image to a colorspace stretched image. In either case, once the false color image and/or the colorspace stretched image is generated, in operation 408, said images may be transmitted back to the damage sizing engine 240 to determine a size of the damage (dent and/or deep scratch). Operation 408 will be described below in greater detail in association with FIG. 10.

Figure 10:
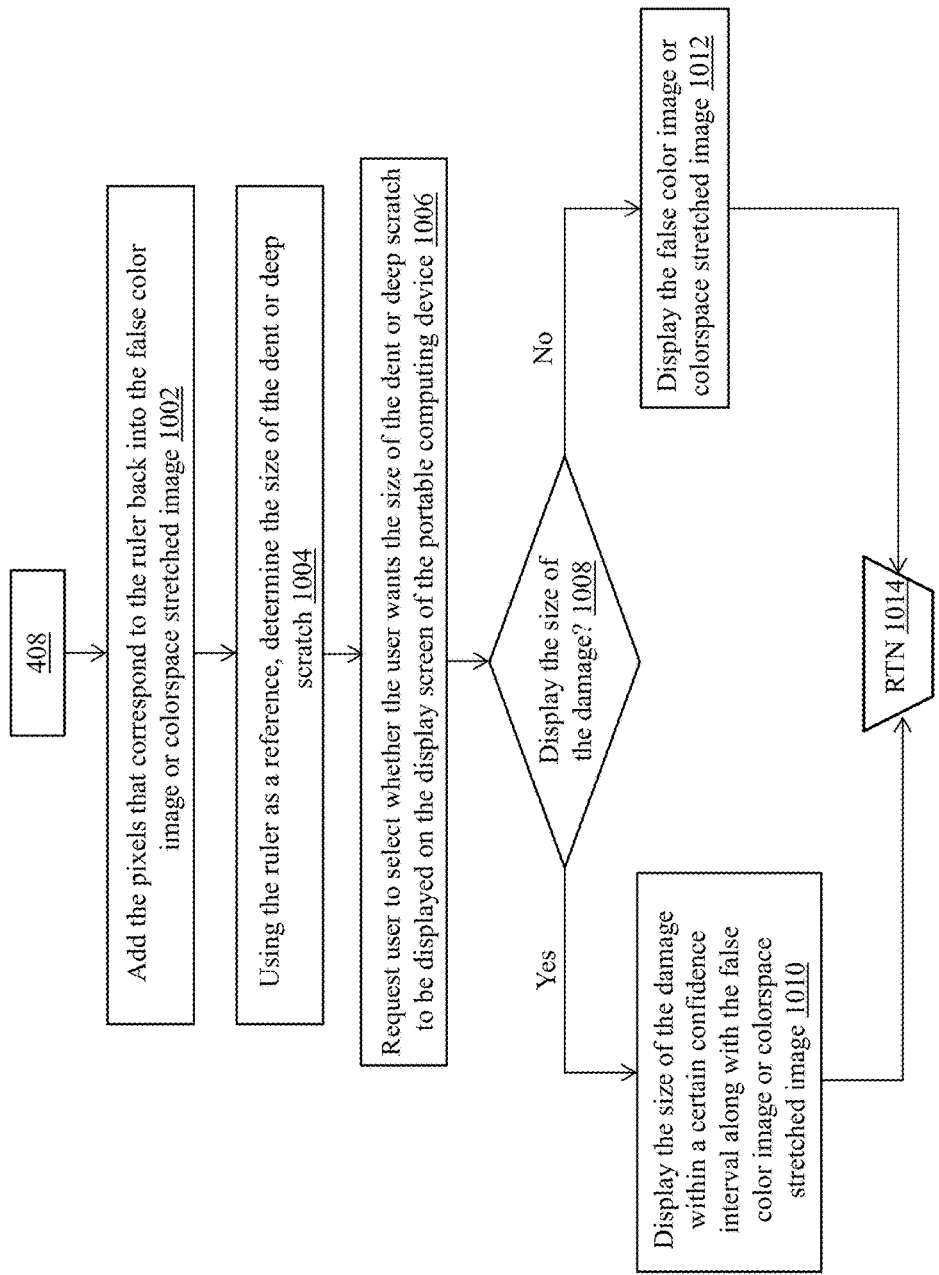
FIG. 10 illustrates a ruler reapplying operation of the damage detection and sizing system, in accordance with example embodiments of the present disclosure.

Turning to FIG. 10, this figure illustrates a ruler reapplying operation of the damage detection and sizing system, in accordance with example embodiments of the present disclosure. Responsive to receiving the false color image and/or the colorspace stretched image from the dent detection engine 210 and/or the deep scratch detection engine 226, respectively, in operation 1002, the ruler reapplying engine 246 adds the pixels corresponding to the ruler (that were cropped out in operation 704) into the false color image or the colorspace stretched image. Example false color images 1402 and 1404 with the ruler are illustrated in FIG. 14. By comparing the final image 1400 to the false color images 1402 and 1404, it can be seen that the dent that is nearly invisible in the final image 1400 is clearly visible (better highlighted) in the false color images 1402 and 1404 that is generated by processing the final image 1400 using the dent detection operation 310. Further, by adding the ruler in the false color images 1402 and 1404 that better highlight the dent, the size of the dent can be determined, which in the example image is $\frac{5}{8}^{th}$ of an inch.

Responsive to adding the ruler to the false color image or the colorspace stretched image, in operation 1004, the damage size determination engine 248 may calculate a size of the damage using the ruler as a reference. For example, as described above in association with FIG. 9, the deep scratch detection engine 226 may determine a start pixel coordinate and an end pixel coordinate of the pixels corresponding to the deep scratch. In operation 1004, the damage size determination engine 248 may use the start and end pixel coordinates in combination with the ruler to determine the length of the deep scratch. Alternatively, as illustrated in FIG. 14, the damage size determination engine 248 may calculate a diameter of a dent (provided dent is substantially circular in shape) by determining the pixel coordinates defining the border of the dent and using it in combination with the ruler. In either case, responsive to determining the size of the dent or the deep scratch, in operations 1006 and 1008, the portable computing device may query the user 108 to determine whether the user 108 wants the size of the damage as determined by the damage size determination engine 248 to be displayed along with the false color image or the colorspace stretched image. If the user 108 wants the size of the damage to be displayed, in operation 1010, the damage sizing engine 240 may coordinate with the dent detection engine 210, the deep scratch detection engine 226, the processor 222, and the display 250 to present the size of the damage within a certain confidence interval along with the false color image or the color space stretched image comprising the ruler. However, if the user 108 does not want the size of the damage to be displayed, then, in operation 1012, only the false color image or the color space stretched image comprising the ruler may be presented to the user 108 via the display 250. Responsive to presenting the false color image, the color space stretched image, and/or the size of the damage within a certain confidence interval, the process returns to operation 410 of FIG. 4 where it ends. Responsive to presenting the false color image, the colorspace stretched image, and/or the size of the damage on the display 250, the user 108 may choose to save said images and the size of the damage or forward said images and the size of the damage to a remote server, such as claims management server, for documenting the damages and/or further analysis.

In the case of a video, one or more images frames of the video may be selected for damage detection processing. Further, each image frame of the one or more image frames may be processed substantially similar to how a single image is processed to detect the dent or damage and/or to estimate a size of the damage as described above in association with FIGS. 3-10.

Figure 11:
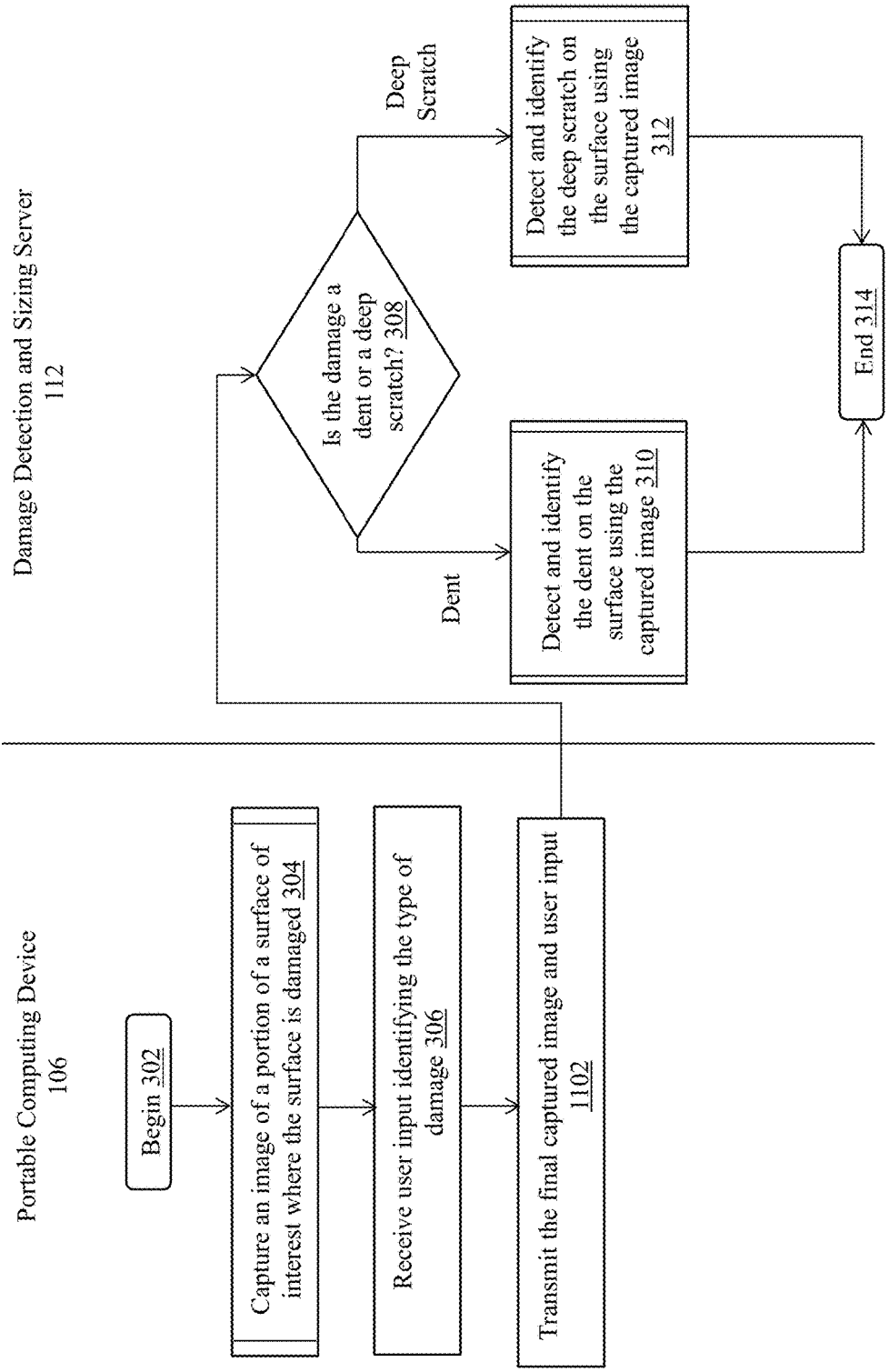
FIG. 11 illustrates an example damage detection operation of the damage detection and sizing system illustrated in FIG. 1A, in accordance with example embodiments of the present disclosure.

Turning to FIG. 11, this figure illustrates an example damage detection operation of the damage detection and sizing system illustrated in FIG. 1B, in accordance with example embodiments of the present disclosure. It is noted that FIG. 11 is substantially similar to FIG. 3 except that the image capture and/or final image generation operations 302-306 are performed at the portable computing device 106 and the damage detection operations 308-314 are performed at a server 112 that is remote from and communicably coupled to the portable computing device 106 via a network 110. Further, operations 302-314 of FIG. 11 have been described above in greater detail in association with FIG. 3 and will not be repeated herein for the sake of brevity. As illustrated in FIG. 11, once the final image has been generated, in operation 1102, the portable computing device 106 may transmit the final image to the server 112 over the network 110 using the wireless transceiver 206. In some example embodiments, the process of generating the final image may also be performed at the server 112. In said example embodiments, instead of the final image, the portable computing device 106 may transmit the one or multiple images of the damaged surface to the server 112.

Figure 12:
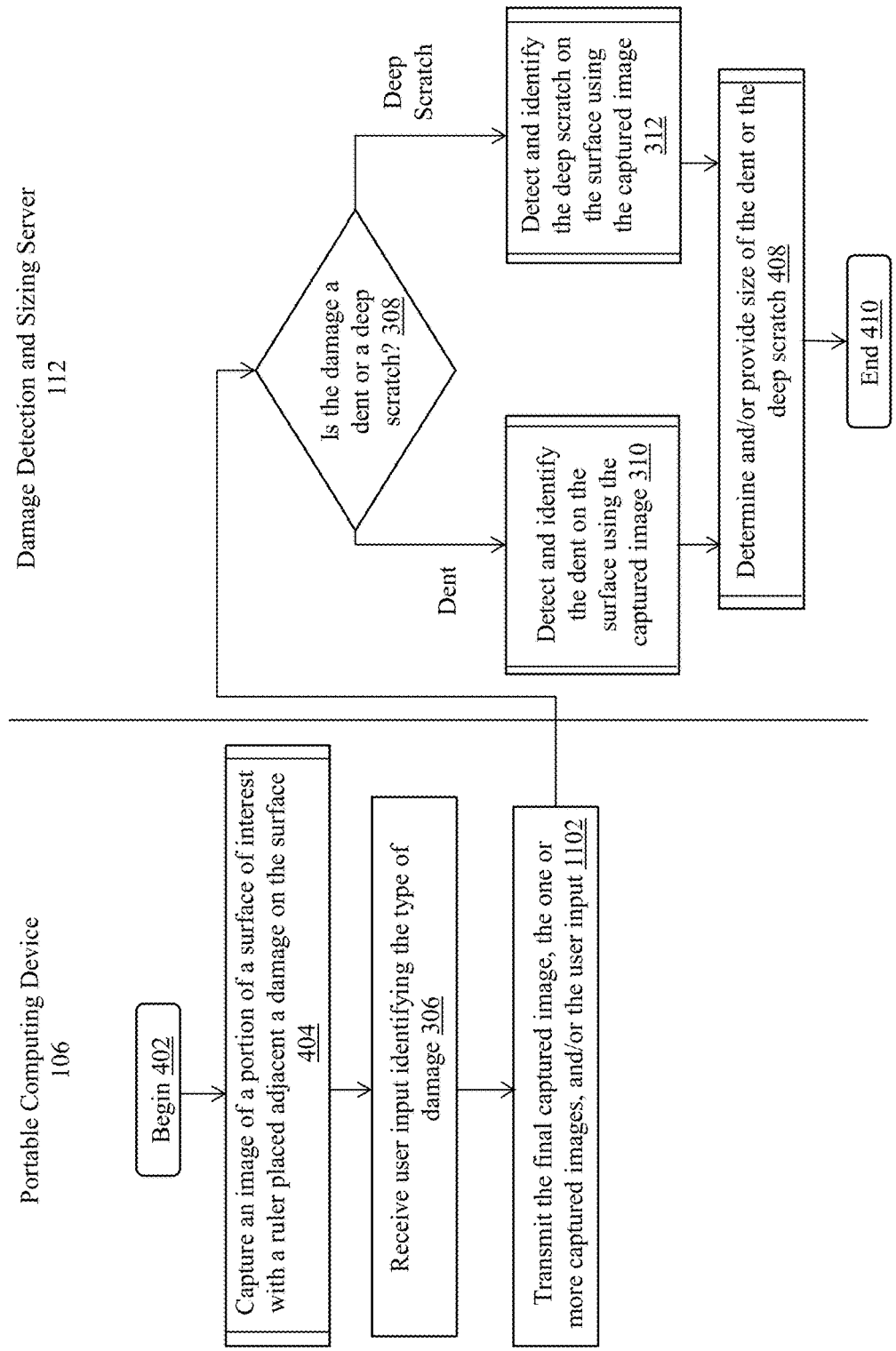
FIG. 12 illustrates an example damage detection and sizing operation of the damage detection and sizing system illustrated in FIG. 1B, in accordance with example embodiments of the present disclosure.

Turning to FIG. 12, this figure illustrates an example damage detection and sizing operation of the damage detection and sizing system illustrated in FIG. 1B, in accordance with example embodiments of the present disclosure. It is noted that FIG. 11 is substantially similar to FIG. 4 except that the image capture and/or final image generation operations 402, 404, and 306 are performed at the portable computing device 106 and the damage detection and sizing operations 406, 308-312, and 408 are performed at a server 112 that is remote from and communicably coupled to the portable computing device 106 via a network 110. Further, operations 402-408 and 306-312 of FIG. 12 have been described above in greater detail in association with FIGS. 3 and 4. Accordingly, said operations will not be repeated herein for the sake of brevity. As illustrated in FIG. 12, once the final image has been generated, in operation 1102, the portable computing device 106 may transmit the final image to the server 112 over the network 110 using the wireless transceiver 206. In some example embodiments, the process of generating the final image may also be performed at the server 112. In said example embodiments, instead of the final image, the portable computing device 106 may transmit the one or multiple images of the damaged surface to the server 112.

It is noted that the system, method, and apparatus described herein is preferably used to detect and determine the size of smaller damages on a surface of interest because larger damages are more evident and visible to the naked eye. However, one of ordinary skill in the art can understand and appreciate that the system, method, and apparatus described herein can also be used to detect and determine size of larger damages on the surface of interest. Further, even though the system, method, and apparatus described herein is used to detect and determine the size of a dent or a deep scratch, one of ordinary skill in the art can understand and appreciate that in other example embodiments, the system, method, and apparatus described herein can be used to detect and determine the size of any other surface depression or change in reflectivity that are not damages but are naturally occurring features and textures of the surface of interest. For example, the texture or rippling of certain fabrics can be highlighted; the markings that are imprinted on plastic products can be read; roughness of tiles, wood, rugs can be highlighted, the dimpling of knobs can be displayed, braille coding on braille books may be highlighted, etc.

Further, even though the present disclosure describes detecting and determining the size of one damage at a time, one of ordinary skill in the art can understand and appreciate that in other example embodiments, the system, method, and apparatus described herein can be used to detect and determine the size of more than one damage at a given time. In said example embodiment, the user 108 may capture an image of a larger portion of the surface of interest having more than one damages. For example, a user may capture an image of an entire side of vehicle. Further, the image may be processed using the dent detection operation 310 or the deep scratch detection operation 312 to generate an output image, e.g., a false color image or a colorspace stretched image, that better highlights the more than one damages. In said vehicle example, the false color image or the colorspace stretched image comprising the entire side of the vehicle and highlighting one or more dents and one or more deep scratches.

Although the present embodiments have been described with reference to specific example embodiments, it will be evident that various modifications and changes may be made to these embodiments without departing from the broader spirit and scope of the various embodiments. For example, the various devices and modules described herein may be enabled and operated using hardware circuitry (e.g., CMOS based logic circuitry), firmware, software or any combination of hardware, firmware, and software (e.g., embodied in a machine readable medium). For example, the various electrical structures and methods may be embodied using transistors, logic gates, and electrical circuits (e.g., application specific integrated (ASIC) circuitry and/or in Digital Signal Processor (DSP) circuitry).

The terms "invention," "the invention," "this invention," and "the present invention," as used herein, intend to refer broadly to all disclosed subject matter and teaching, and recitations containing these terms should not be misconstrued as limiting the subject matter taught herein or to limit the meaning or scope of the claims. From the description of the exemplary embodiments, equivalents of the elements shown therein will suggest themselves to those skilled in the art, and ways of constructing other embodiments of the present invention will appear to practitioners of the art. Therefore, the scope of the present invention is to be limited only by the claims that follow.

In addition, it will be appreciated that the various operations, processes, and methods disclosed herein may be embodied in a machine-readable medium and/or a machine accessible medium compatible with a data processing system (e.g., a computer system), and may be performed in any order (e.g., including using means for achieving the various operations). Accordingly, the specification and drawings are to be regarded in an illustrative rather than a restrictive sense.

What is claimed is:

1. A system comprising:
a handheld portable computing device that comprises at least one image capture device, wherein the portable computing device is configured to:
capture, using the at least one image capture device, one or more images of a portion of a surface of interest that has a damage;
receive a user input identifying a type of the damage;
responsive to identifying the type of damage as a dent based on the user input,
generate, using the one or more captured images, a final image having an optimal reflection pattern;
blur the final image by removing high frequency edge components of the final image; and
generate, using the blurred image and a saliency algorithm, an output image in which less salient features of the blurred image are damped and more salient features of the blurred image are enhanced, wherein the less salient features include reflections from the surface of interest and the more salient features include the dent on the surface of interest; and
present the output image via a display of the portable computing device.

2. The system of claim 1, wherein the surface of interest is a reflective surface.

3. The system of claim 1, wherein the portable computing device further comprises an assistive light source, wherein light from the assistive light source is directed towards the portion of the surface that has the damage prior to capturing the one or more images.

4. The system of claim 1, wherein to capture the one or more images of the portion of the surface of interest that has the damage, the portable computing device is configured to:
process an image feed received by the image capture device to compensate for variable lighting conditions including natural light and artificial light;
render the processed image feed on the display of the portable computing device; and
generate and overlay one or more graphical cues on the rendered image feed in the display, wherein the one or more graphical cues are configured to provide guidance on how to position the image capture device to optimize reflection patterns in the one or more images.

5. The system of claim 1, wherein the output image is a false color image that highlights the dent.

6. The system of claim 1, wherein to generate the output image using the blurred image and the saliency algorithm, the portable computing device is configured to:
generate a saliency map comprising saliency values of each pixel of the blurred image by applying the saliency algorithm on the blurred image;
normalize the saliency values of each pixel in the saliency map; and
multiply the normalized saliency values of each pixel that exceed a threshold saliency value with corresponding pixels of the blurred image to generate the output image,
wherein the output image is a false color image.

7. The system of claim 1, wherein when the type of damage is a deep scratch, the portable computing device is configured to transform the one or more captured images to a colorspace stretched image that highlights the deep scratch.

8. A system comprising:
a handheld portable computing device that comprises at least one image capture device, wherein the portable computing device is configured to:
capture, using the at least one image capture device, one or more images of a portion of a surface of interest that has a damage;
receive a user input identifying a type of the damage;
responsive to identifying the type of damage as a deep scratch based on the user input, a deep scratch detection engine of the handheld portable computing device is configured to:
transform the one or more captured images to a colorspace stretched image, wherein to transform the one or more capture images to a colorspace stretched image, a pixel density enhancing engine of the handheld portable computing device is configured to generate a final image having an enhanced resolution using the one or more captured images; and a colorspace stretching engine of the handheld portable device is configured to stretch a colorspace of the final image to define an edge of the deep scratch in more detail within the final image;
process, by a color gradient detection engine, the colorspace stretched image to determine a color gradient in the colorspace stretched image;
determine that pixels of the colorspace stretched image that correspond to the color gradient are within a threshold narrow band of pixels; and
responsively, identify the pixels corresponding to the color gradient as the deep scratch; and
present the colorspace stretched image via a display of the portable computing device.

9. A system for detecting and sizing a damage on a reflective surface comprising:
a portable computing device that comprises a video capture device, an assistive light source, a processor, a display, and a wireless transceiver, wherein the portable computing device is configured to:
capture, using the video capture device, a video of a portion of the reflective surface having the damage and a ruler positioned adjacent the damage, wherein the ruler and the portion of the reflective surface having the damage are exposed to a light from the assistive light source;
receive a user input identifying a type of the damage; and
transmit the user input and the video; and
a server that is communicably coupled to the portable computing device via a network, wherein the server configured to:
receive the user input and the video from the wireless transceiver of the portable computing device;
responsive to receiving the video and based on the type of the damage, generate a set of final images from the video;
identify the ruler in the set of final images based on a geometry and/or a color of the ruler;
remove pixels corresponding to the ruler from the set of final images to form a modified set of final images;
based on the type of the damage, transform the modified set of final images to an output image that highlights the damage on the reflective surface;
add the pixels corresponding to the ruler to the output image;
calculate the size of the damage highlighted in the output image comprising the ruler using the ruler as reference; and
transmitting the output image comprising the ruler and the calculated size of the damage to the portable computing device for visual representation on the display.

10. The system of claim 9, wherein to capture the video of the portion of the reflective surface having the damage, the portable computing device is configured to:
process an image feed received by the at least one video capture device to compensate for variable lighting conditions including an intensity of a natural light and an intensity of an artificial light;
render the processed video feed on the display of the portable computing device; and
generate and overlay one or more graphical cues on the rendered video feed in the display, wherein the one or more graphical cues are configured to provide guidance on how to position the video capture device to optimize reflection patterns in the video.

11. The system of claim 9, wherein when the type of damage is a dent, a dent detection engine of the server is configured to transform the modified set of final images to a false color image that highlights the dent.

12. The system of claim 11, wherein to transform the modified set of final images to a false color image that highlights the dent, the dent detection engine is configured to:
blur the modified set of final images by removing high frequency edge components;
generate a saliency map comprising saliency values of each pixel of the modified set of final images that are blurred by applying a saliency algorithm on the blurred set of final images;
normalize the saliency values of each pixel in the saliency map;
multiply the normalized saliency values of each pixel of each final image of the modified set of final images that are blurred that exceeds a threshold saliency value with the corresponding pixels of the respective final image to generate a set of false color images that highlights the dent; and
select the false color image from the set of false color images for presentation.

13. The system of claim 12, wherein in each false color image, less salient features are damped and more salient features are enhanced, and wherein the less salient features include reflections from the surface of interest and the more salient features include the dent on the surface of interest.

14. The system of claim 9, wherein when the type of damage is a deep scratch, to generate the set of final images, a deep scratch detection engine of the server is configured to process one or more image frames of the video by superimposing each image frame of the one or more image frames with its neighboring image frames to create the set of final images having enhanced resolution.

15. The system of claim 9, wherein when the type of damage is a deep scratch, a deep scratch detection engine of the server is configured to transform the modified set of final images to a colorspace stretched image that highlights the deep scratch.

16. The system of claim 15, wherein to transform the modified set of images to a colorspace stretched image that highlights the deep scratch, the deep scratch detection engine is configured to:
stretching a colorspace of each modified final image to generate a set of colorspace stretched images, each colorspace stretched image defining an edge of the deep scratch in more detail;
processing each colorspace stretched image to determine a color gradient in the respective colorspace stretched image;
determining that pixels of each colorspace stretched image corresponding to the color gradient are within a threshold narrow band of pixels and that the pixels are aligned in a line;
identifying the pixels corresponding to the color gradient as a deep scratch; and
selecting the colorspace stretched image from the set of colorspace stretched images.

17. A portable computing device that is configured to detect and size a damage on a surface of interest, the portable computing device comprising:
a flash that is configured to direct artificial light towards a portion of the surface of interest that has the damage and a ruler that is placed adjacent the damage;
a camera that is configured to capture one or more images of the portion of the surface of interest that has the damage along with the ruler that is placed adjacent to the damage;
a dent detection engine that is configured to:
create, using the one or more captured images, a final image having an optimal reflection pattern; and
responsive to identifying a ruler in the final image based on a geometry and/or a color of the ruler and removing pixels corresponding to the ruler from the final image by a damage sizing engine of the portable computing device, convert the final image to a false color image that highlights the dent;
a deep scratch detection engine that is configured to:
create another final image having an enhanced resolution by superimposing the one or more captured images;
responsive to identifying a ruler in the other final image based on a geometry and/or a color of the ruler and removing pixels corresponding to the ruler from the other final image by a damage sizing engine of the portable computing device, convert the other final image to a colorspace stretched image that highlights the deep scratch,
wherein the damage sizing engine is configured to add the pixels corresponding to the ruler to at least one of the false color image and the colorspace stretched image, and wherein the damage sizing engine is configured to calculate a size of at least one of the dent and the deep scratch using the ruler as a reference;
a display that is configured to visually present at least one of the false color image, the colorspace stretched image, the size of the dent, and the size of the deep scratch based on a type of the damage.

18. The portable computing device of claim 17, wherein the surface of interest is a reflective surface.

19. The portable computing device of claim 17, wherein to convert the final image to the false color image, the dent detection engine is configured to:
blur the final image by removing high frequency edge components of the final image;
generate a saliency map comprising saliency values of each pixel of the blurred image by applying a saliency algorithm on the blurred image;
normalize the saliency values of each pixel in the saliency map; and
multiply the normalized saliency values of each pixel that exceed a certain threshold with corresponding pixels of the blurred image to generate the false color image in which less salient features of the blurred image are damped and more salient features of the blurred image are enhanced, wherein the less salient features include reflections from the surface of interest and the more salient features include the dent on the surface of interest.

20. The portable computing device of claim 17, wherein to convert the other final image to the colorspace stretched image, the deep scratch detection engine is configured to:
stretch a colorspace of the final image to define an edge of the deep scratch in more detail within the final image;
process the colorspace stretched image to determine a color gradient in the colorspace stretched image;
determine that pixels of the colorspace stretched image corresponding to color gradient are within a threshold narrow band of pixels and that the pixels are aligned in a line; and
identify the pixels corresponding to the color gradient as a deep scratch.

21. A system comprising:
a handheld portable computing device that comprises at least one image capture device, wherein the portable computing device is configured to:
  capture, using the at least one image capture device, one or more images of a portion of a surface of interest that has a damage;
  process the one or more captured images by a dent detection engine and a deep scratch detection engine of the portable computing device in parallel;
  convert, by the dent detection engine using a saliency algorithm, the one or more captured images to a false color image in which less salient features are damped and more salient features are enhanced, wherein the less salient features include reflections from the surface of interest and the more salient features include the damage on the surface of interest;
  convert, by the deep scratch detection engine, the one or more captured images to a colorspace stretched image;
  determine a type of the damage based on whether the dent detection engine or the deep scratch detection engine provides a positive identification of the damage; wherein when the dent detection engine provides the positive identification of the damage, the damage is a dent, and wherein when the deep scratch detection engine provides the positive identification of the damage, the damage is a deep scratch;
  present at least one of the false color image and the colorspace stretched image via a display of the portable computing device.

22. The system of claim 21, wherein to convert the one or more captured images to the false color image, the dent detection engine is configured to:
  generate, using the one or more captured images, a final image having an optimal reflection pattern;
  blur the final image by removing high frequency edge components of the final image;
  generate a saliency map comprising saliency values of each pixel of the blurred image by applying a saliency algorithm on the blurred image;
  normalize the saliency values of each pixel in the saliency map; and
  multiply the normalized saliency values of each pixel that exceed a certain threshold with the corresponding pixels of the blurred image to generate the false color image in which less salient features of the blurred image are damped and more salient features of the blurred image are enhanced, wherein the less salient features include reflections from the surface of interest and the more salient features include the dent on the surface of interest.

23. The portable computing device of claim 21, wherein to convert the one or more captured images to the colorspace stretched image, the deep scratch detection engine is configured to:
  determine if a pixel density of the one or more captured images is less than a threshold pixel density value;
  responsive to a determining that the pixel density of the one or more captured images is less than the threshold pixel density value, creating a final image having an enhanced resolution by superimposing the one or more captured images;
  responsively, stretching a colorspace of the final image to define an edge of the deep scratch in more detail within the final image;
  processing the colorspace stretched image to determine a color gradient in the colorspace stretched image;
  determining that pixels of the colorspace stretched image corresponding to the color gradient are within a threshold narrow band of pixels and that the pixels are aligned in a line; and
  identifying the pixels corresponding to the color gradient as a deep scratch.

24. The system of claim 8:
wherein to generate the final image having the enhanced resolution, the pixel density enhancing engine is configured to:
  determine if a pixel density of the one or more captured images is less than a threshold pixel density value, and
  responsive to a determining that the pixel density of the one or more captured images is less than the threshold pixel density value, superimpose the one or more captured images to generate the final image, and
wherein to identify the pixels corresponding to the color gradient as the deep scratch,
  the deep scratch detection engine is configured to:
    determine that the pixels of the colorspace stretched image that correspond to the color gradient are aligned in a line.

* * * * *